(12) United States Patent
Cullen

(10) Patent No.: US 11,224,387 B2
(45) Date of Patent: Jan. 18, 2022

(54) DIGITAL DENTAL X-RAY SENSOR DEVICE HAVING A ROUNDED HOUSING

(71) Applicant: Shayda Cullen, Tampa, FL (US)

(72) Inventor: Shayda Cullen, Tampa, FL (US)

( * ) Notice: Subject to any disclaimer, the term of this patent is extended or adjusted under 35 U.S.C. 154(b) by 0 days.

(21) Appl. No.: 17/225,858

(22) Filed: Apr. 8, 2021

(65) Prior Publication Data

US 2021/0307706 A1 Oct. 7, 2021

Related U.S. Application Data

(63) Continuation-in-part of application No. 16/715,826, filed on Dec. 16, 2019, which is a continuation-in-part of application No. 16/162,080, filed on Oct. 16, 2018, now Pat. No. 10,506,992.

(51) Int. Cl.
*A61B 6/14* (2006.01)
*A61B 6/00* (2006.01)

(52) U.S. Cl.
CPC ............ *A61B 6/145* (2013.01); *A61B 6/4429* (2013.01); *A61B 6/563* (2013.01)

(58) Field of Classification Search
CPC .......... A61B 6/145; A61B 5/0088; A61B 6/14; A61B 6/42; A61B 6/4208; A61B 6/563; A61B 6/4429
See application file for complete search history.

(56) References Cited

U.S. PATENT DOCUMENTS

| | | | |
|---|---|---|---|
| 7,959,355 B2 * | 6/2011 | Stantchev | A61B 6/4435 378/191 |
| 2006/0067462 A1 * | 3/2006 | Hack | A61B 6/145 378/38 |
| 2016/0324491 A1 * | 11/2016 | Kim | A61B 6/145 |
| 2016/0361037 A1 * | 12/2016 | Im | A61B 6/5217 |
| 2018/0064405 A1 * | 3/2018 | Miller | A61B 6/145 |

* cited by examiner

*Primary Examiner* — David P Porta
*Assistant Examiner* — Mamadou Faye
(74) *Attorney, Agent, or Firm* — The Concept Law Group, PA; Scott D. Smiley; Scott M. Garrett

(57) ABSTRACT

A digital dental x-ray sensor device includes a rounded, three-dimensional housing that lacks corners, edges, or other relatively sharp features that are known to cause discomfort when used in a patient's mouth. The rounded housing can be spherical, ellipsoid, or any similar regular or irregular rounded shape, and can be formed by ensuring that all curves of the surface of the rounded housing have a minimum radius that is sufficient to prevent features that can dig into the soft tissue of the inside of a patient's mouth.

20 Claims, 30 Drawing Sheets

DIGITAL DENTAL X-RAY SENSOR DEVICE HAVING A ROUNDED HOUSING

CROSS REFERENCE

This application is a continuation in part of application Ser. No. 16/715,826, filed Dec. 16, 2019, which is a continuation in part of application Ser. No. 16/162,080, filed Oct. 16, 2018, now U.S. Pat. No. 10,506,992, the entireties of each of which are hereby incorporated by reference.

FIELD OF THE INVENTION

The present invention relates generally to dental x-ray sensors, and, more particularly, relates to a dental x-ray sensor device that fits comfortably in a person's mouth, and which allows broader angles of view to be taken by an x-ray compared to conventional x-ray sensors.

BACKGROUND OF THE INVENTION

Dentists have been using x-ray photography to examine teeth and dental work for decades. In the past a slide of film was placed in a protective rectangular sheath and put into a patient's mouth. These sheaths had uncomfortable edges and corners that contributed to the general unpleasantness associated with a visit to a dentist's office. Typically the corners and edges would dig into the patient's soft palate in the roof of their mouth, as well as in the lower jaw around the tongue. For some patients, particularly children, the shape of x-ray film sheaths made it very difficult to obtain good images.

More recently, the film x-ray has been replaced by digital x-ray sensors. Digital x-ray sensors use conventional image sensor technology, such a complementary metallic oxide semiconductor (CMOS) image sensors, in combination with a scintillator that produces visible light in the presence of x-rays, to produce a digital image. However, these digital x-ray sensors have retained the conventional rectangular form factor, and most of the uncomfortableness associated with that form factor.

The rectangular cuboid/prism shape of conventional digital x-ray sensors can cause mild to extreme discomfort in some patients. Among the issues experienced by dental patients, people report that the x-ray sensor produces a "cutting" sensation on the inside of their mouth, the feeling of being "smothered," as well as inducing a gag reflex which can lead to vomiting. Different people have different sized mouths, so a large sensor for adults can still be difficult to accommodate by some adults with smaller mouths.

Therefore, a need exists to overcome the problems with the prior art as discussed above.

SUMMARY OF THE INVENTION

The invention provides a digital dental x-ray sensor device that overcomes the hereinafore-mentioned disadvantages of the heretofore-known devices and methods of this general type and that can be used comfortably by patients without the irritation and uncomfortableness associated with prior art dental x-ray sensors.

Embodiments of the inventive disclosure provide a dental x-ray sensor device that includes a rounded housing configured fit in a patient's mouth that is configured to contain a digital x-ray sensor having a front, the rounded housing having an external surface lacking edges or corners. The rounded housing can include a flat face that is circular or elliptical that corresponds to a plane of a digital x-ray sensor configured to be mounted in the rounded housing. The dental x-ray sensor device can further include a handle attachment feature formed on an outside surface of the rounded housing that is that is positioned to be in front of the digital x-ray sensor, and which allows attachment of a handle at a plurality of positions along the handle attachment feature.

In accordance with another feature, the rounded housing comprises a first and a second portion that are configured to separably couple together and which provide a sensor bed configured to receive a rectangular digital x-ray sensor.

In accordance with another feature, the rounded housing is semi-spherically shaped.

In accordance with another feature, the rounded housing is configured to contain a circular digital x-ray sensor that conforms to an internal cross section of the rounded housing, and wherein the dental x-ray sensor device further comprises the circular digital x-ray sensor.

In accordance with another feature, the handle attachment feature comprises a groove that is configured to receive a base of a coupling member having detent features, and wherein the groove has a plurality of corresponding detent features at positions along the groove.

In accordance with another feature, the rounded housing has an external surface having a minimum radius of five millimeters.

In accordance with another feature, the rounded housing comprises an indicia that indicates an orientation of the digital x-ray sensor inside the rounded housing.

In accordance with some aspects of the inventive disclosure, some embodiments can provide a digital dental x-ray sensor device including a rounded housing having an external surface that lacks edges and corners and that is configured to fit with a person's mouth with the person's mouth substantially closed. The rounded housing comprises a flat face that is circular or elliptical that corresponds to a plane of a digital x-ray sensor configured to be mounted in the rounded housing. The device can further include a digital x-ray sensor disposed within the rounded housing that conforms to an internal cross section of the rounded housing. The device can also include an attachment feature on an exterior of the rounded housing that is configured to receive a coupling member in a channel of the attachment feature.

In accordance with another feature, the rounded housing is a semi-spherical housing.

In accordance with another feature, the semi-spherical housing includes a shoulder.

In accordance with another feature, the rounded housing is an ellipsoid.

In accordance with another feature, the rounded housing comprises at least one flat spot.

In accordance with another feature, the digital x-ray sensor has a circular shape.

In accordance with another feature, the attachment feature is positioned on the rounded housing in front of the digital x-ray sensor.

In accordance with another feature, the attachment features comprises a plurality of detent features, each one of the plurality of detent features corresponding to a respective position along the channel and configured to mate with a corresponding detent feature on the coupling member.

In still some other embodiments of the inventive disclosure, there is provided a digital dental x-ray sensor system that includes a digital dental x-ray sensor device having a rounded housing, a digital x-ray sensor disposed within the rounded housing, and an attachment feature formed on an exterior of the rounded housing. The rounded housing comprises a flat face that is circular or elliptical that corresponds to a plane of a digital x-ray sensor configured to be mounted in the rounded housing. The system can further include a coupling member having a portion configured to fit within a channel of the attachment feature and be moveably retained in the channel, and having a head portion connected to the portion configured to fit within the channel. The system can further include a handle member having a first end configured to attach to the head of the coupling member, and having a second end opposite the first end. The system can further include a coupling ring configured to be retained on an emitter portion of an x-ray source, and having an extension that extends from a track formed on the coupling ring that is configured to attach to the second end of the handle member.

In accordance with another feature, the rounded housing is semi-spherical.

In accordance with another feature, the digital x-ray sensor is circular.

In accordance with another feature, the channel of the attachment feature comprises a plurality of detent features, where each one of the detent features is corresponds to a respective one of a plurality of positions along the channel, and the portion of the coupling member is configured to fit with the channel includes corresponding detent features to mate with the plurality of detent features in the channel to hold the coupling member at one of the plurality of positions along the channel.

In accordance with another feature, the extension of the coupling ring is movable along the track to hold the extension at a selected position along the track.

Although the invention is illustrated and described herein as embodied in a digital dental x-ray sensor and system, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

As defined herein, the term "corner" refers to a point location on a surface where two or more planes of the surface meet. The term "edge" refers to a continuous line or curve along the meeting of two planes or faces of a surface. Furthermore, an edge can be rounded, having a radius of curvature of less than five millimeters and generally where two planes or faces of a surface meet at an angle of more than forty five degrees.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. Those skilled in the art can understand the specific meanings of the above-mentioned terms in the embodiments of the present invention according to the specific circumstances. Furthermore, it will be appreciated by those skilled in the art that the features of the various embodiments shown in the various drawings can be combined among the embodiments shown in the drawings.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
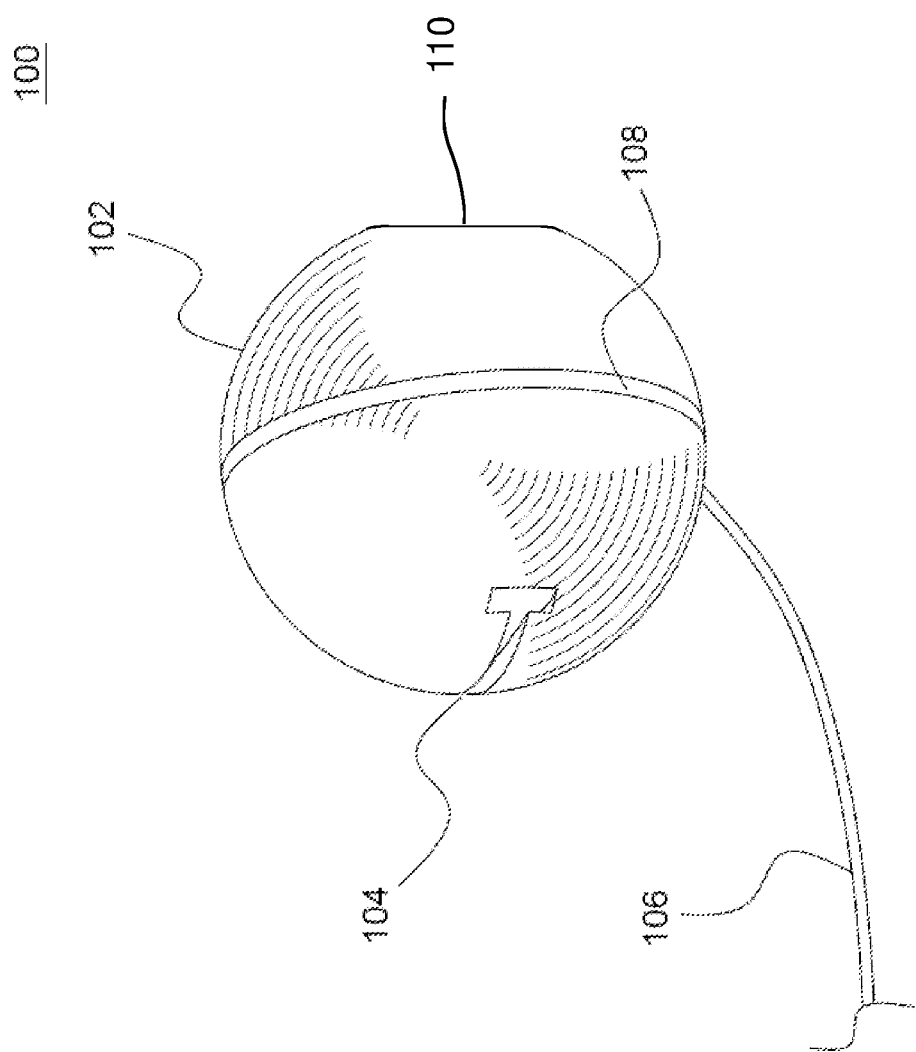
FIG. 1 is a digital x-ray sensor device having a rounded housing, in accordance with some embodiments.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

Embodiments of the present inventive disclosure provide a novel and efficient digital dental x-ray sensor device that is configured to alleviate the problems associated with conventional digital dental x-ray sensors. In particular, embodiments provide a rounded housing that has no corners, points, or edges that would cause pain in the soft tissue of a patient's mouth. Furthermore, the rounded housing reduces triggering a gag reflex in some patients who may otherwise be susceptible to gagging when using conventional digital dental x-ray sensors. In addition, the inventive disclosure provides features for adjusting the attachment location of the digital x-ray sensor device to a handle that can be connected to an x-ray source in order to optimize the position of the digital x-ray sensor in the patient's mouth for a given x-ray image.

FIG. 1 is a digital x-ray sensor device 100 having a rounded housing 102, in accordance with some embodiments. The digital x-ray sensor device 100 is a device used to produce dental x-ray images while avoiding the problems associated with conventional, rectangular x-ray sensors. The digital x-ray sensor device 100 is used by placing it in the mouth of a patient, orienting it properly, and directing a beam of x-ray emissions towards the digital x-ray sensor device 100. The digital x-ray sensor device 100 produces a digital image of the patient's teeth, gums, and supporting bone in response to the x-ray emissions.

Many patients have experienced discomfort in using conventional rectangular prismatic dental x-ray sensors due to the corners and edges of these conventional sensors, which can result in discomfort ranging from mild pain to inducing a gag response or even vomiting. To reduce the discomfort experienced by patients, the digital x-ray sensor device 100 includes a rounded housing 102, meaning the external surface of the rounded housing 102 is rounded, and lacks corners, protrusions, or edges that could dig into the patient's soft tissue, particularly at the top and bottom of the rounded housing 102. Furthermore, the rounded housing 102 lacks any regions where two planar faces meet to form an edge. In some embodiments the rounded body can include one or more isolated planar faces 110 having a perimeter that meets rounded surfaces (e.g. a flat spot). In some embodiments, the rounded housing 102 can be spherical in shape, although not necessarily a perfect sphere. The rounded housing 102 can be an eccentric or irregular spheroid or ellipsoid (e.g. egg-shaped), having a width or length that is longer or shorter than dimensions in other directions, or it can include external surface feature such as bulges or depressions in some places. In some embodiments the rounded housing can have a flattened face on the external surface that is aligned (e.g. parallel) to a plane of an x-ray image sensor inside the digital x-ray sensor device 100. In some embodiments the rounded housing 102 can have a flat spot to prevent the digital x-ray sensor device 100 from rolling when not in use and sitting on a surface. Although the rounded housing 102 can occupy more volume in a patient's mouth than a conventional rectangular prism shaped sensor, the rounded housing 102 eliminates any features that could dig into, or otherwise contact, the patent's soft tissue inside the patient's mouth, and cause the type of discomfort associated with the conventional x-ray sensor form factors. In some embodiments the rounded housing can have features with convex curves having a radius of not less than five millimeters over the majority of the external surface of the rounded housing. Some features may be present in locations that will not be against the patient's soft tissue in their mouth that have a smaller curve radius.

The rounded housing 102 is provided with an attachment feature 104 to allow the rounded housing 102 to couple to a handle or support member that is used to properly align the digital x-ray sensor device 100 in the patient's mouth. A cable 106 is connected to the internal circuitry of the digital x-ray sensor device 100 and allows transmission of instruction and information to and from the digital x-ray sensor device 100, including the transmission of image data from the digital x-ray sensor device 100 to an image rendering computer system. An external indicia 108, such as a line or other indicia, can further be provided on an outside of the rounded housing 102 to indicate an orientation of the digital x-ray sensor device 100, and specifically an orientation of the image sensor housing inside the rounded housing 102 to allow the technician or clinician to properly orient the digital x-ray sensor device 100 device with respect to the particular teeth being x-rayed. In some embodiments the attachment feature can be located in front of the internal image sensor housing within the rounded housing 102, meaning the attachment feature 104 will be between the x-ray source and the internal image sensor.

The attachment feature 104 can be a groove or channel formed in the surface of the rounded housing 102 that is configured to receive a coupling member which has a portion that fits within, and is retained by, the groove or channel. The attachment feature 104 can include structure that allows the coupling member to be positioned at various locations in the attachment feature 104 to achieve slightly different orientations of the digital x-ray sensor device 100 relative to the patient's teeth and an x-ray emitter located outside the patient. Thus, the attachment feature 104 can be used to optimally align and position the digital x-ray sensor device 100 to produce x-ray images of particular desired views of the patient's dental environment.

Figure 2:
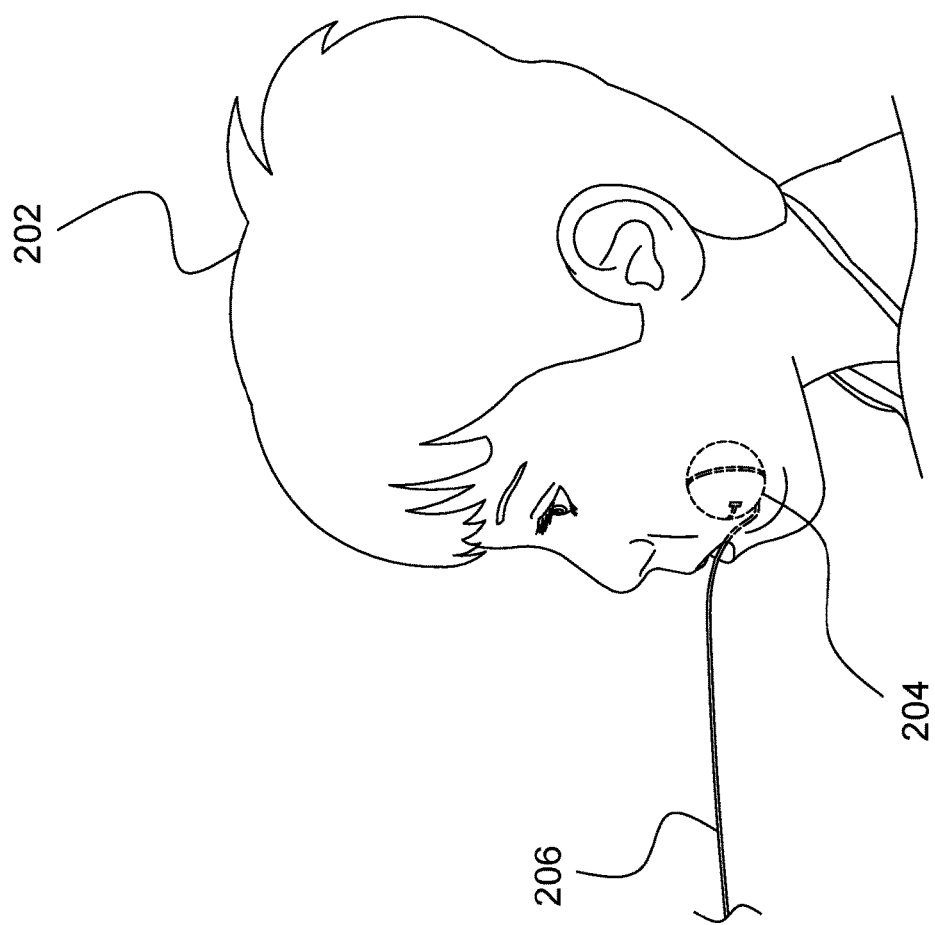
FIG. 2 is a side view of a patient having a dental x-ray taken while using a digital x-ray sensor device, in accordance with some embodiments.

FIG. 2 is a side view 200 of a patient 202 having a dental x-ray taken while using a digital x-ray sensor device 204, in accordance with some embodiments. The digital x-ray sensor device 204 is hidden from view as being inside the mouth of the patient 202, so the digital x-ray sensor device 204 is represented here in broken line. The digital x-ray sensor device 204 can be substantially similar to the digital x-ray sensor device 100 of FIG. 1. A technician can place the digital x-ray sensor device 204 in the mouth of the patient 202 in a proper orientation in cooperation with an external x-ray emitter source (not shown), as is known. The data cable 206 connected to the digital x-ray sensor device 204 passes out of the mouth of the patient 202 to an image rendering system.

Figure 3:
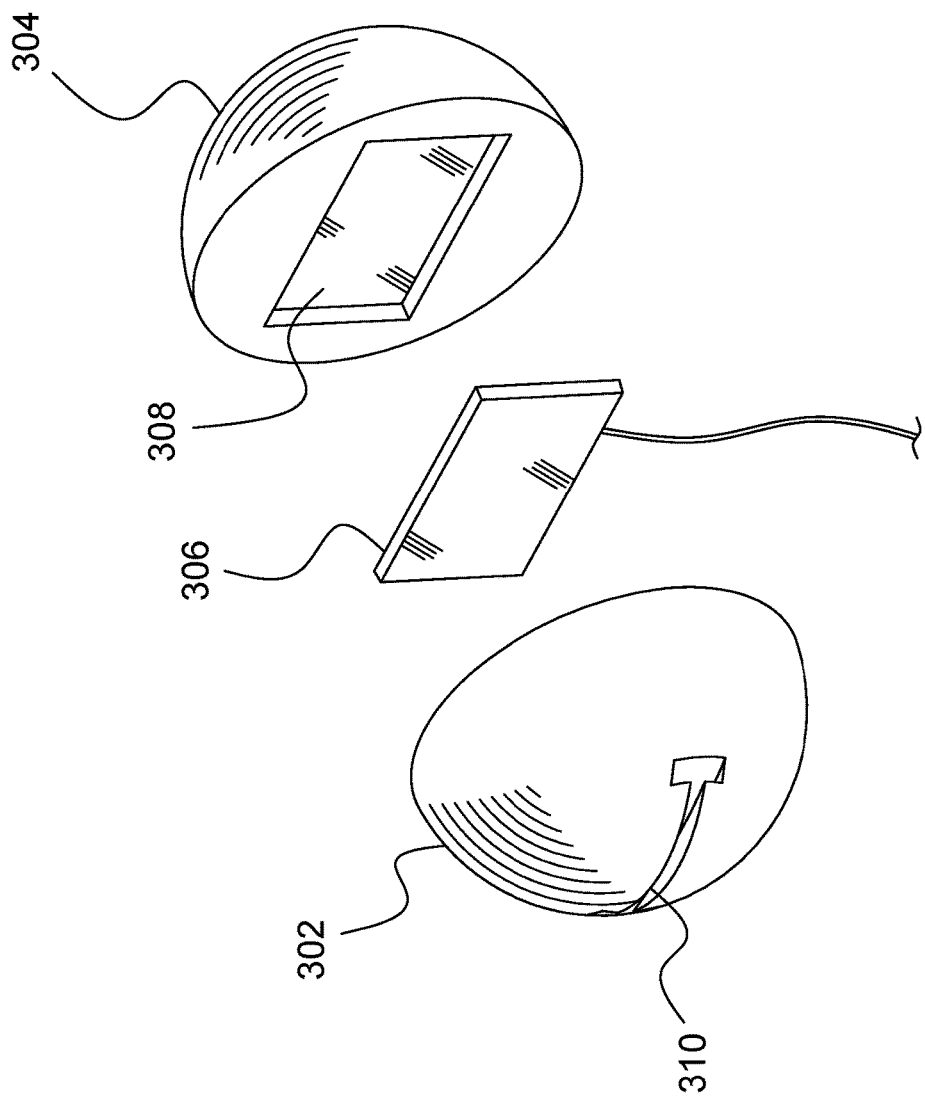
FIG. 3 is an exploded perspective view of a digital x-ray sensor device having a rounded housing for containing a conventional digital x-ray sensor, in accordance with some embodiments.

FIG. 3 is an exploded perspective view of a digital x-ray sensor device 300 having a rounded housing for containing a conventional rectangular digital x-ray sensor 306, in accordance with some embodiments. The housing can be comprised of two halves, such as a first half 302 and a second half 304. The housing portions 302, 304 can produce a sphere, ellipsoid, irregular sphere or ellipsoid, or other rounded shapes. The conventional rectangular digital x-ray sensor 306 can be held inside the housing portions 302, 304 in a bed 308 that is a physical arrangement that supports and holds the rectangular digital x-ray sensor 306 in place. In some embodiments, the bed 308 can include different bedding orientations to hold rectangular sensors of different sizes. The housing portions 302, 304 can couple together in a way that they are held together (e.g. with retention features) but which allow a technician to take them apart for cleaning, and use with other rectangular x-ray sensors. As in FIG. 1, the housing portions 302, 304 can include an attachment feature 310 on an external surface that allows coupling to a handle member. The conventional digital x-ray sensor 306 can be, for example, the type that is presently in use, including a polymeric external housing, or it can be a specially adapted housing including all of the sensor components and circuitry that could be used in conventional applications with a conventional housing.

Figure 4:
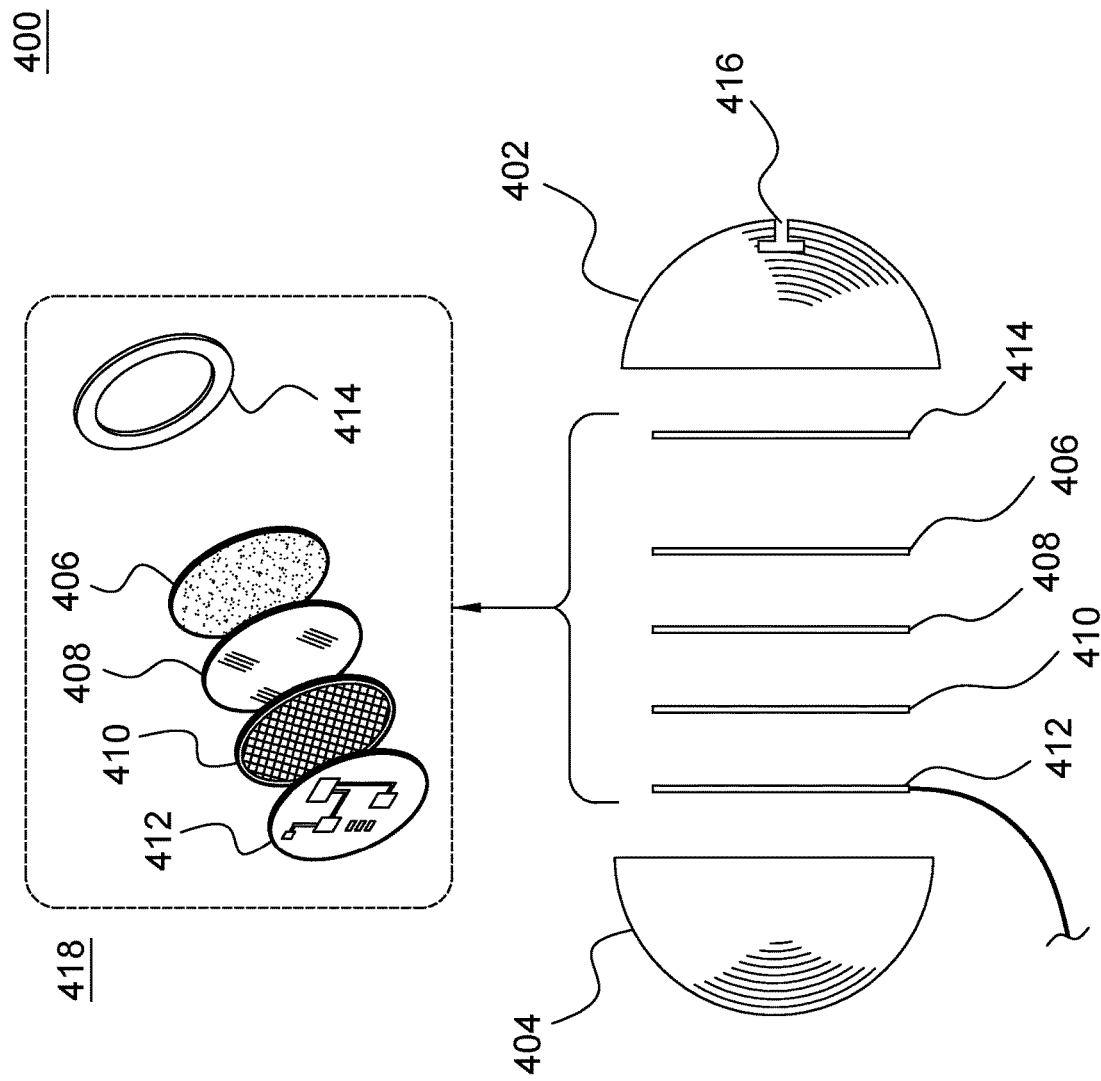
FIG. 4 is a side elevational exploded view of a digital x-ray sensor device having a rounded housing for containing a round digital x-ray sensor, in accordance with some embodiments.

FIG. 4 is a side elevational exploded view of a digital x-ray sensor device 400 having a rounded housing for containing a circular digital x-ray sensor, in accordance with some embodiments. The rounded housing can be comprised of housing portions 402, 404 which provide a rounded external surface in the shape of a sphere or other rounded surface, as described in reference to FIG. 1. The housing portions 402, 404 can be permanently, semi-permanently, or removably joined together, and provide an attachment feature 416. The housing portions 402, 404 house a digital x-ray sensor comprised of a stack of components that includes a scintillator 406, a fiber optic lensing array 408, a digital image sensor 410, and a circuit board 412. In some embodiments an annular shock pad 414, made of a compressible resilient material, can be provided as well to absorb mechanical shock experienced by the assembled device 400 to protect the other sensor components 406-412, which are shown in a perspective view detail 418.

The scintillator 406 is reactive to x-ray emissions and produces visible light in response, and in proportion to the intensity of the x-rays incident on the scintillator 406. Light produced by the scintillator 406 is directed through a fiber optic lensing array 408 to an image sensor 410. The lensing array 408 is comprised of segments of optical fiber placed in parallel in the plane of the lensing array 408 to direct light from the scintillator 406 to the image sensor 410, and to prevent bleeding of light from one portion of the scintillator 406 to adjacent portions of the image sensor 410. The image sensor can be a CMOS image sensor that converts light intensity to a digital value corresponding to the light intensity at each of a plurality of pixel locations, as is known. The circuit board 412 includes control and power circuitry to drive and operate the image sensor 410, and further includes data communication circuitry to transmit image data to a connected image rendering system (e.g. a computer).

The scintillator 406 is at the front of the stack, meaning it is closest to the x-ray source in use, and defines a front plane that is to be oriented in the direction of the x-ray source. Accordingly, the x-rays emitted from the x-ray source, when the digital x-ray sensor is correctly oriented for use, travel approximately perpendicular to the front plane of the scintillator 406.

In perspective detail 418, it can be seen that the sensor stack components 406-414 are substantially circular, or otherwise having a perimeter that conforms to the shape of the internal cross section space of the housing portions 402, 404. This arrangement reduces the unused area that remains when using a rectangular sensor, as in FIG. 4. With a substantially circular sensor configuration, the angle at which the digital x-ray sensor 400 is turned when placed in a patient's mouth is less relevant than with rectangular x-ray sensors.

Figure 5:
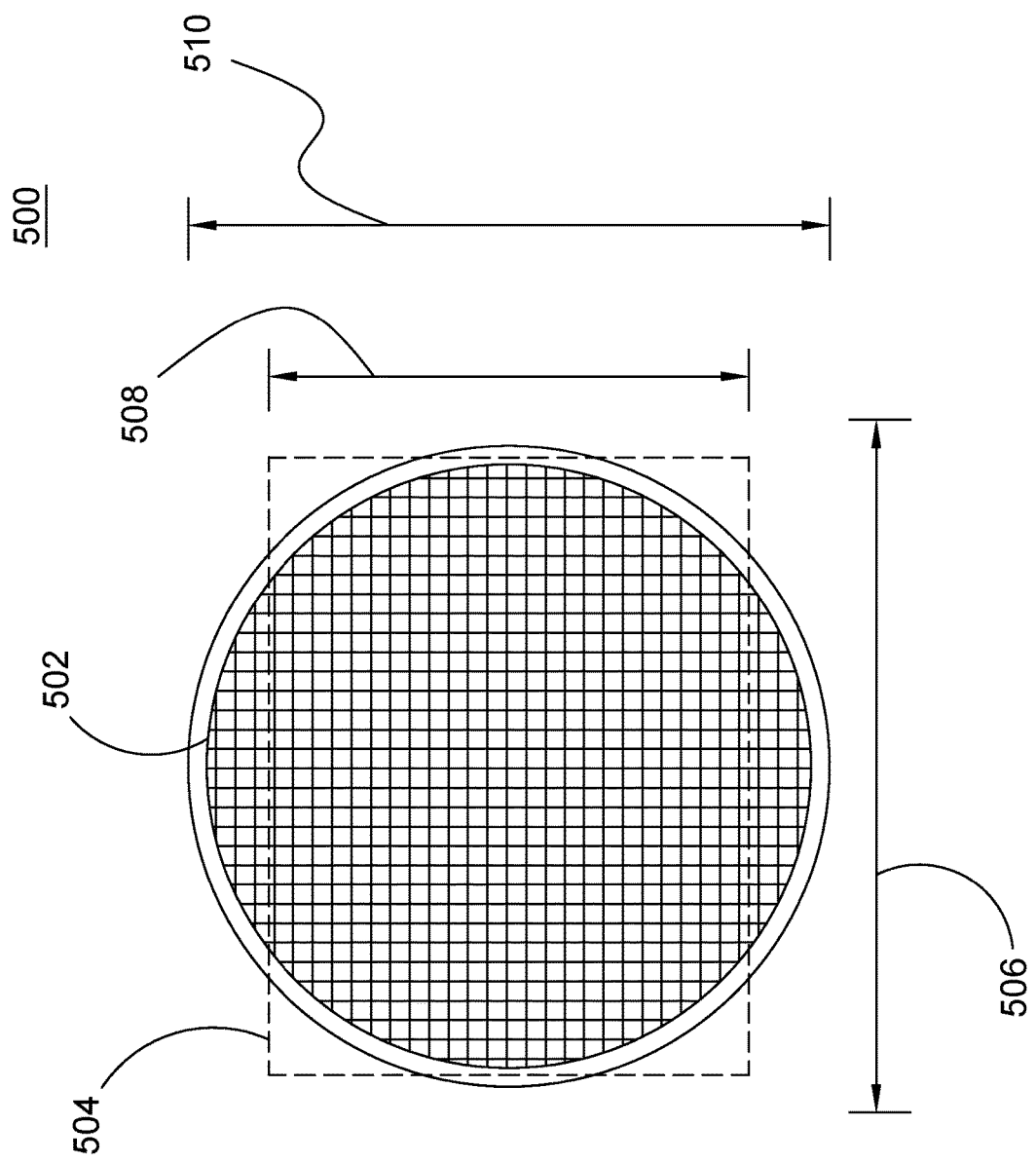
FIG. 5 is a front view of a round digital x-ray sensor, in accordance with some embodiments.

FIG. 5 is a front view 500 of a round digital x-ray sensor 502, in accordance with some embodiments. The round digital x-ray sensor 502 can be used in rounded digital x-ray sensor devices such as those shown in FIGS. 1 and 4. The x-ray sensor 500 can include all of the components 406-412 of FIG. 4. One advantage of the round/circular configuration is that the area of the circle maximizes the image area while also making it less crucial to have the top and bottom of the sensor aligned with the direction of the patient's teeth. For comparison, a rectangular x-ray sensor of a conventional size is projected over the circular x-ray sensor 502 in outline 504. The rectangular x-ray sensor projection 504 has a width dimension 506 that is equivalent to the diameter of the circular x-ray sensor 502, and a height dimension 508 that is only a portion of the height/diameter 510 of the circular x-ray sensor 502. However, the height 510 of the circular x-ray sensor 502 is also equal to its diameter, providing more image area above and below the rectangular projection, which can be regions of interest in dental x-rays. The corner regions of the rectangular projection 504 fall outside of the circular area of the circular x-ray sensor, but it is not typical to have image content of interest in these corner regions using conventional rectangular x-ray sensors.

Figure 6:
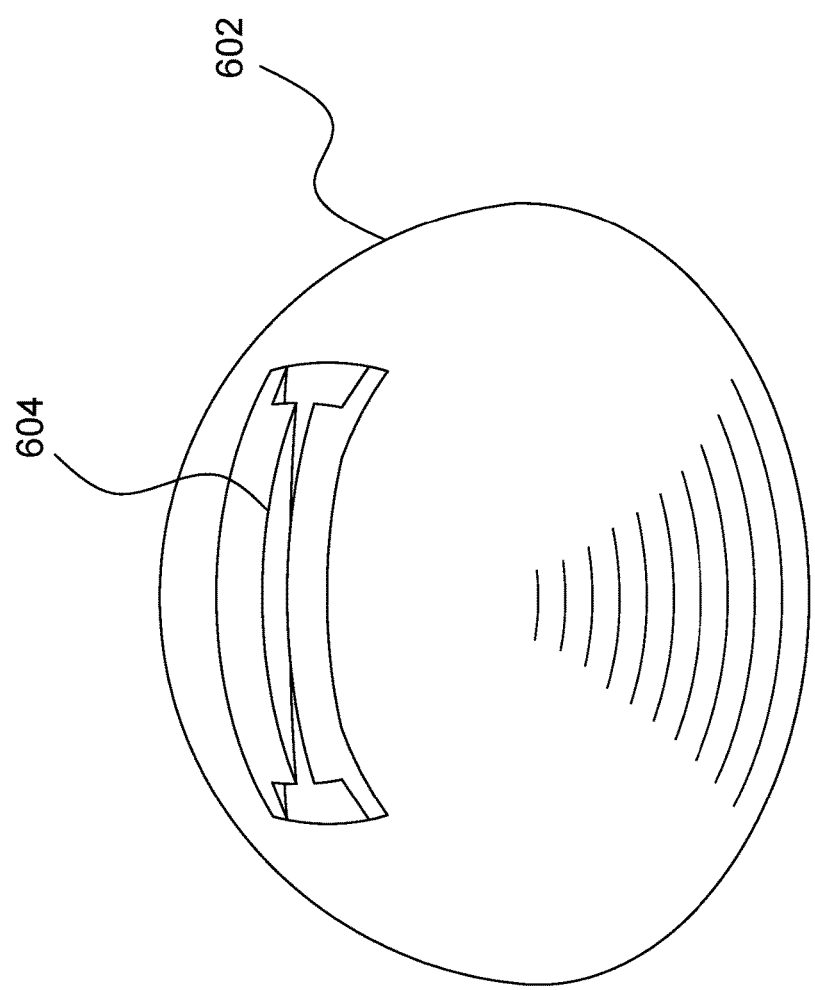
FIG. 6 is a side perspective view of a portion of a rounded housing of a digital x-ray sensor device with an attachment feature for coupling to a handle member, in accordance with some embodiments.
Figure 7:
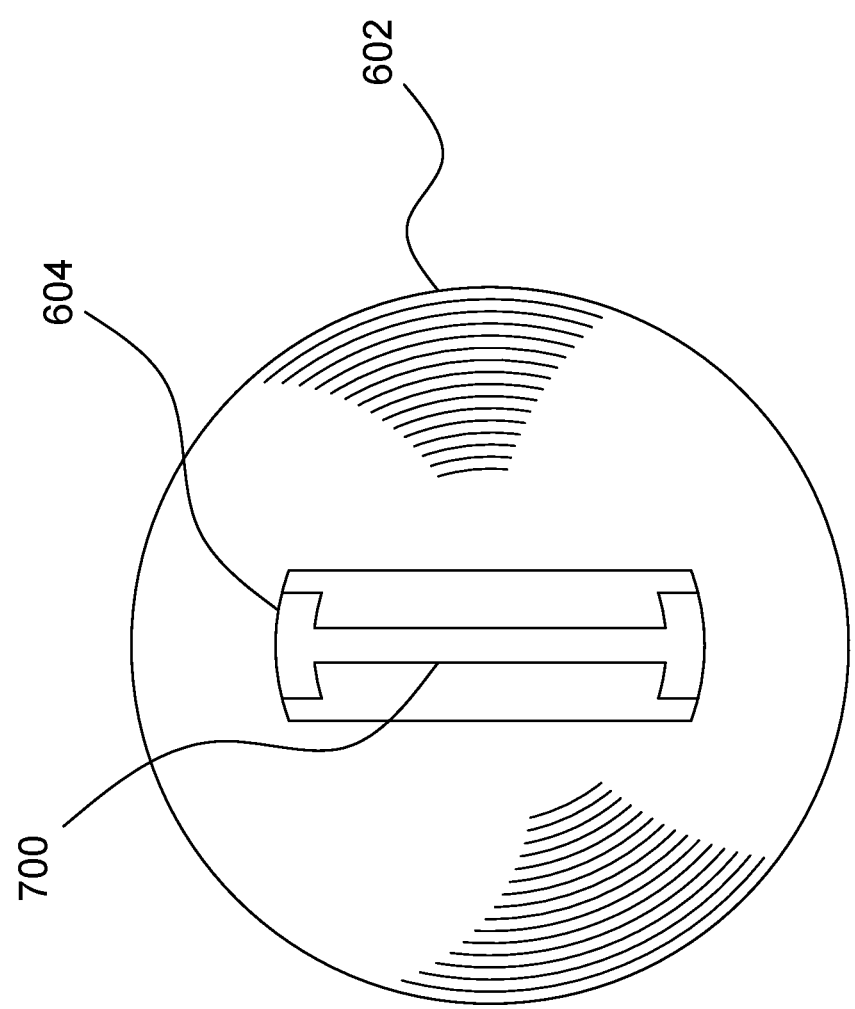
FIG. 7 is a front view of digital x-ray sensor device showing an attachment feature for coupling to a handle member, in accordance with some embodiments.
Figure 8:
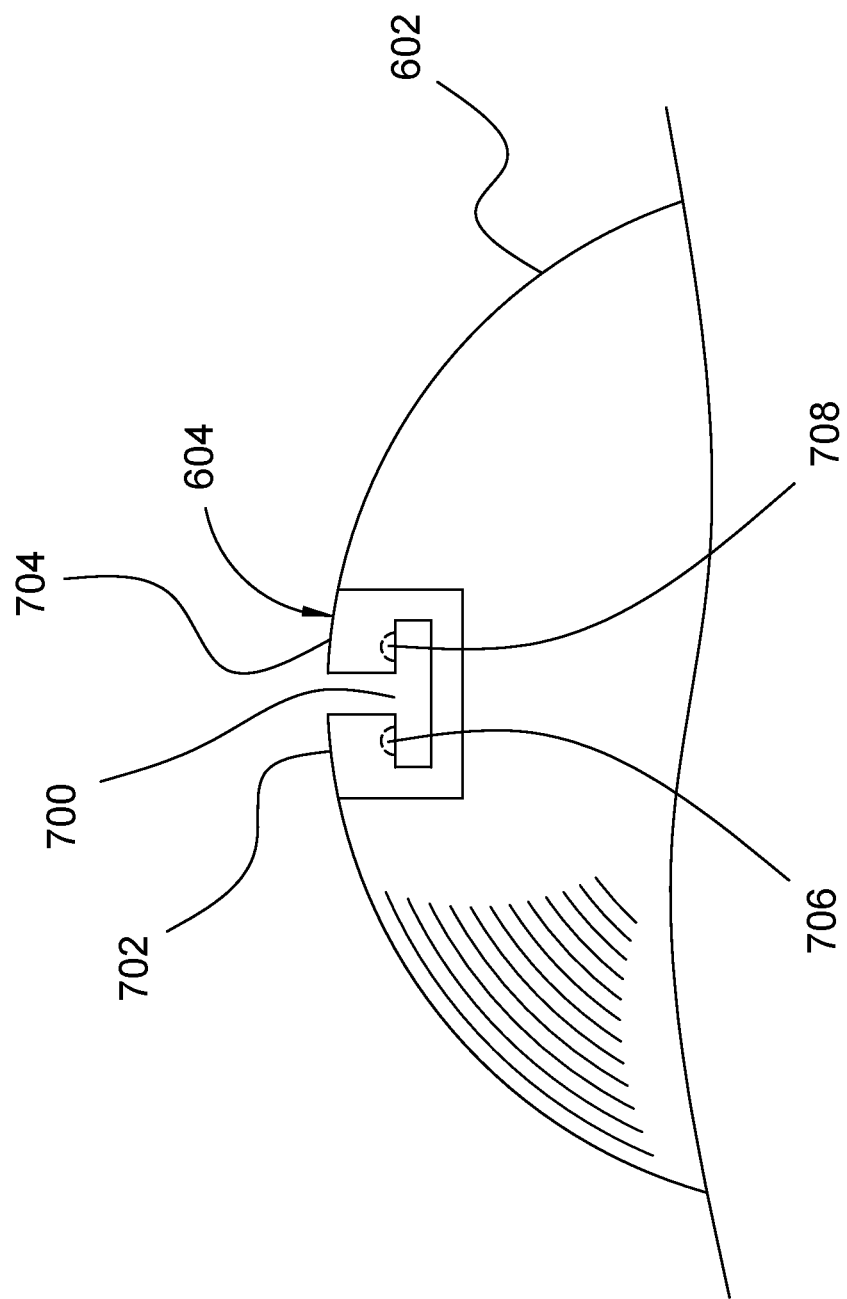
FIG. 8 is a side view of an attachment feature on the rounded housing of a digital x-ray sensor, in accordance with some embodiments.

FIGS. 6-8 show various view of a rounded housing for a digital x-ray sensor device, specifically showing detail of the attachment feature. FIG. 6 shows a side perspective view of a portion of a rounded housing of a digital x-ray sensor device; FIG. 7 shows a front view of digital x-ray sensor device; and FIG. 8 shows a side cut-away view of an attachment feature, looking along the channel of the attachment feature, on the rounded housing of a digital x-ray sensor.

A portion 600 of a rounded housing of a digital x-ray sensor includes an external surface 602 in which an attachment feature 604 is formed. As will be appreciated by those skilled in the art, there are numerous equivalent structures that can be used to couple a handle member to the rounded housing. In one example of an attachment feature 604, a channel or groove 700 is formed in the external surface 602. The channel 700 can include overhang or shoulder portions 702, 704 on either side of the channel 700 that capture a portion of a coupling member in the channel 700. The shoulder portions 702, 704 can have detent features 706, 708 at positions along the channel 700 to hold the coupling member at those positions, while also allowing the coupling member to be moved to different positions in the channel 700. The distance between the bottom of the shoulder portions 702, 704, in the channel 700, and the external surface of the housing 602 can be constant and follow the curve of the external surface over the shoulder portions 702, 704, or it can be straight through the housing, having a varying distance between the bottom of the shoulder portions 702, 704 and the external surface 602, However, the distance between the bottom of the shoulder portions 702, 704 and the bottom the channel 700 will be substantially constant along the channel to accommodate the base of the coupling member that is placed in the channel 700.

The detent features 706, 708 can be depressions formed in the bottom of the shoulder portions 702, 704 in some embodiments that correspond with complementary detent features in the coupling member. In some embodiments different detent features may be equivalently used. In some embodiments there can be detents corresponding to several positions along the channel 700 to accommodate different mouth shapes. For example, in some embodiments there can be five positions including a top, middle top, middle, middle bottom, and bottom. This allows the technician/clinician to adjust the position of the digital x-ray sensor device so that it sits comfortably in the patient's mouth while still being able to orient the digital x-ray sensor device to obtain the desired x-ray image.

Figure 9:
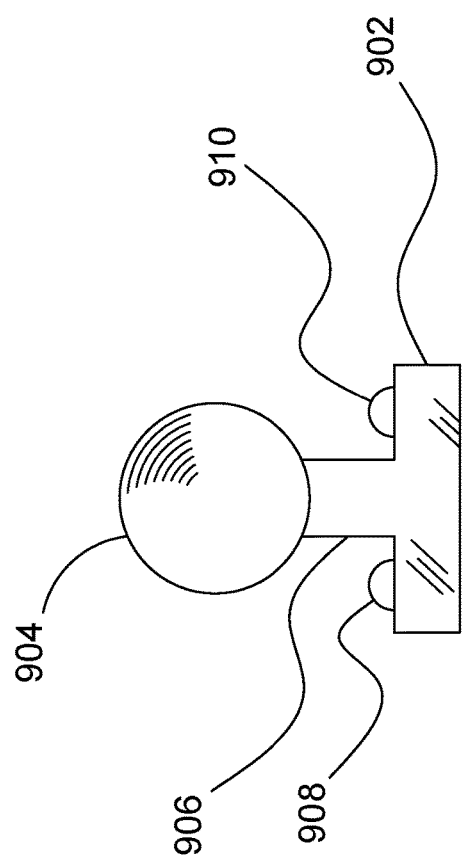
FIG. 9 shows a side view of a coupling member for coupling a handle member to an attachment feature of a digital x-ray sensor, in accordance with some embodiments.

FIG. 9 shows a side view of a coupling member 900 for coupling a handle member to an attachment feature of a digital x-ray sensor, in accordance with some embodiments. The coupling member 900 can be used in conjunction with the attachment feature of FIGS. 6-8, for example. The coupling member 900 includes a base portion 902 that is configured to be captured in channel 700, under shoulders 702, 704. A shaft portion 906 is configured to extend upwards from the base portion 902 between shoulders 702, 704, with detent features 908, 910 being configured to mate with detent features 706, 708. On top of the shaft portion is a ball-shaped head 904 that is configured to mate with a handle member is a ball and socket coupling arrangement.

Figure 10:
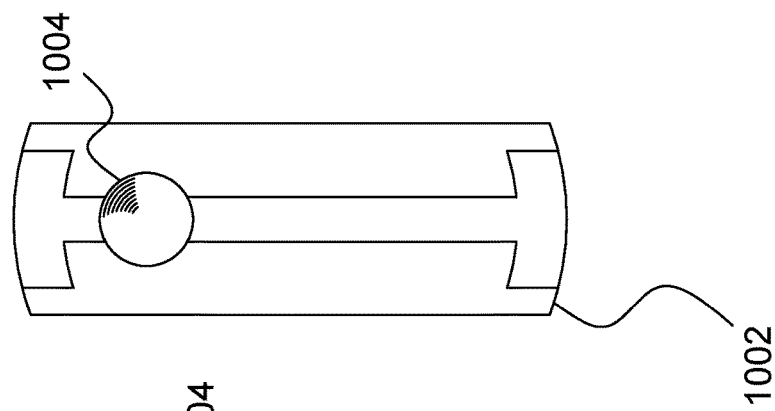
FIG. 10 shows a series of views from the front of a digital x-ray sensor device illustrating how a coupling member can be moved to different positions in the attachment feature of the digital x-ray sensor device, in accordance with some embodiments.
Figure 10:
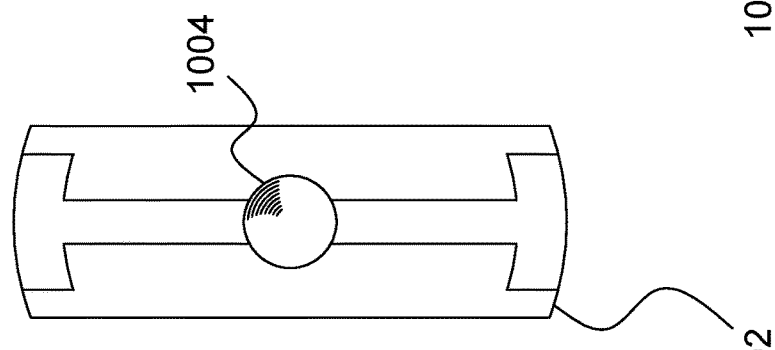
Figure 10:
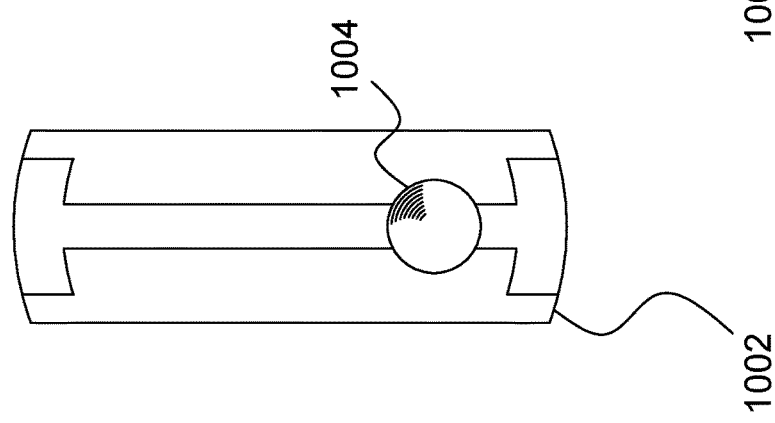

FIG. 10 shows a series of views from the front of a digital x-ray sensor device illustrating how a coupling member 1004 can be moved to different positions in the attachment feature 1002 of the digital x-ray sensor device, in accordance with some embodiments. The attachment feature 1002 is shown with a head of a coupling member 1004 in three different exemplary positions 1006, 1008, 1010 which correspond to different detent locations. The attachment feature 1002 and the coupling member 1004 can be substantially similar to attachment feature 604 of FIGS. 6-8 and coupling member 900 of FIG. 9, respectively. Position 1006 shows the coupling member 1004 closer to a first end of the attachment feature 1002. Position 1008 shows the coupling member 1004 in the middle of the attachment feature 1002. Position 1010 shows the coupling member 1004 near a second end of the attachment feature 1002. A technician can select any of the available positions provided on an attachment feature to optimize the orientation and position of the digital x-ray sensor device in the patient's mouth for producing an x-ray image.

Figure 11:
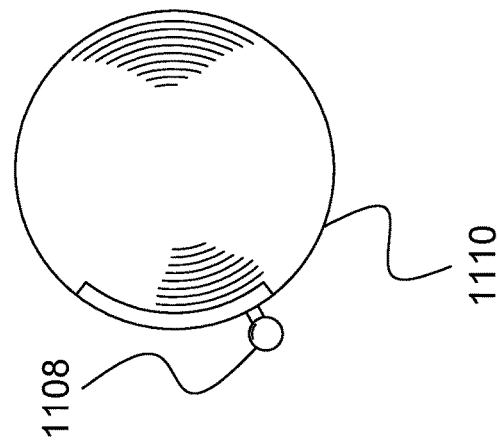
FIG. 11 a series of views from the side of a digital x-ray sensor device illustrating how a coupling member can be moved to different positions in the attachment feature of the digital x-ray sensor device, in accordance with some embodiments.
Figure 11:
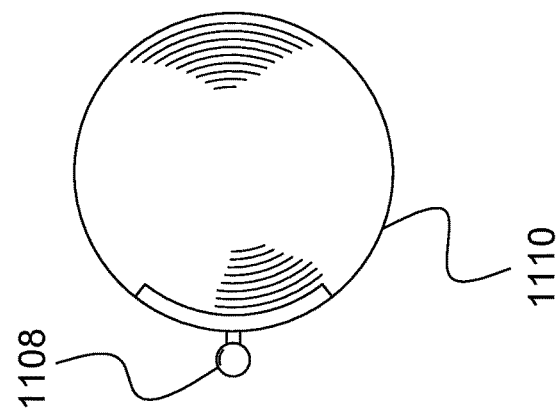
Figure 11:
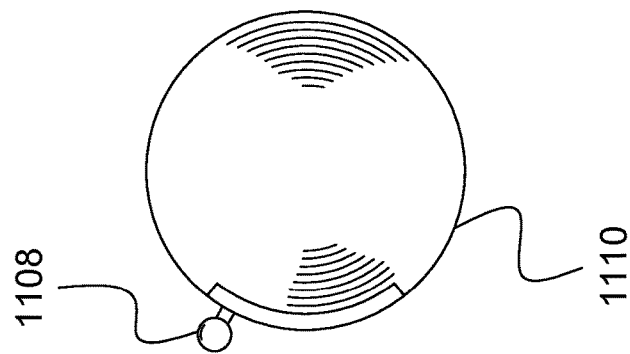
Figure 13:
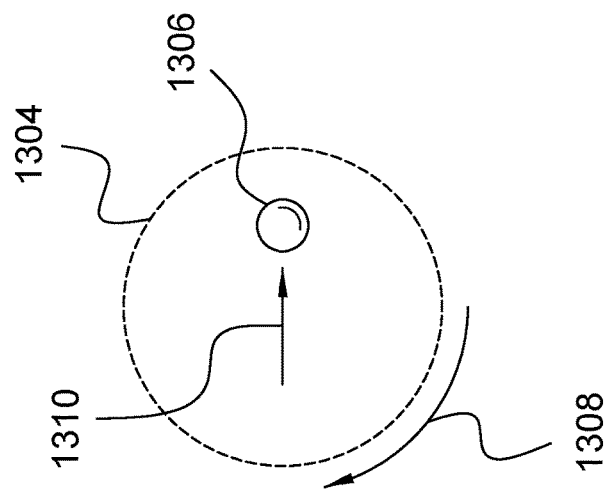
FIG. 13 shows a front projection view of a coupling member is different positions relative to a digital x-ray sensor, in accordance with some embodiments.
Figure 13:
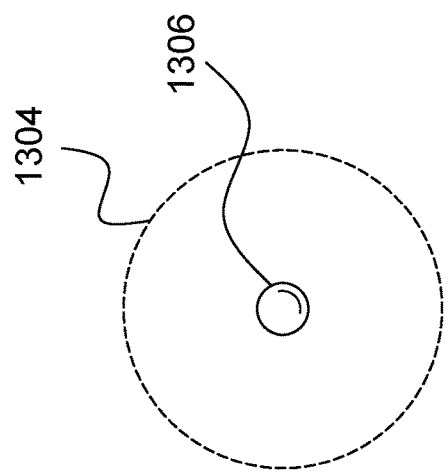

FIG. 11 a series of views 1102, 1104, 1106 from the side of a digital x-ray sensor device 1110 illustrating how a coupling member 1108 can be moved to different positions in the attachment feature of the digital x-ray sensor device, in accordance with some embodiments. The views 1102, 1104, 1106 can correspond to positions 1006, 1008, 1010, respectively, of FIG. 10. The digital x-ray sensor device 1110 includes a rounded housing, and can be designed substantially in accordance with the digital x-ray sensor device of FIG. 1, for example. FIG. 13 shows the effect of moving the coupling member to different locations in the attachment feature of the digital x-ray sensor device in two views 1300, 1302. In both views 1300, 1302 the front of a circular x-ray sensor 1304 (in broken line) is facing the outwards from the page, and the viewer's perspective is from approximately the location of an x-ray source that would be used with the digital x-ray sensor 1304. In view 1300 the coupling member 1306 is centered over the front of the circular x-ray sensor 1304, corresponding with 1008 and 1104 of FIGS. 10 and 11, respectively. In this position the circular image sensor 1304 is equally above and below the point where the patient's upper and lower teeth meet. In view 1302 the coupling member 1304 is moved to the side, as indicated by arrow 1310, resulting in a larger portion of the circular digital x-ray sensor being positioned to the left of the coupling member 1306. This position can be used, for example, when imaging the molar teeth of the patient. Thus, the attachment point, at the coupling member, can be used to adjust the position of the digital x-ray sensor in a given patient's mouth, for a particular x-ray image, and make it more comfortable for the patient.

Figure 12:
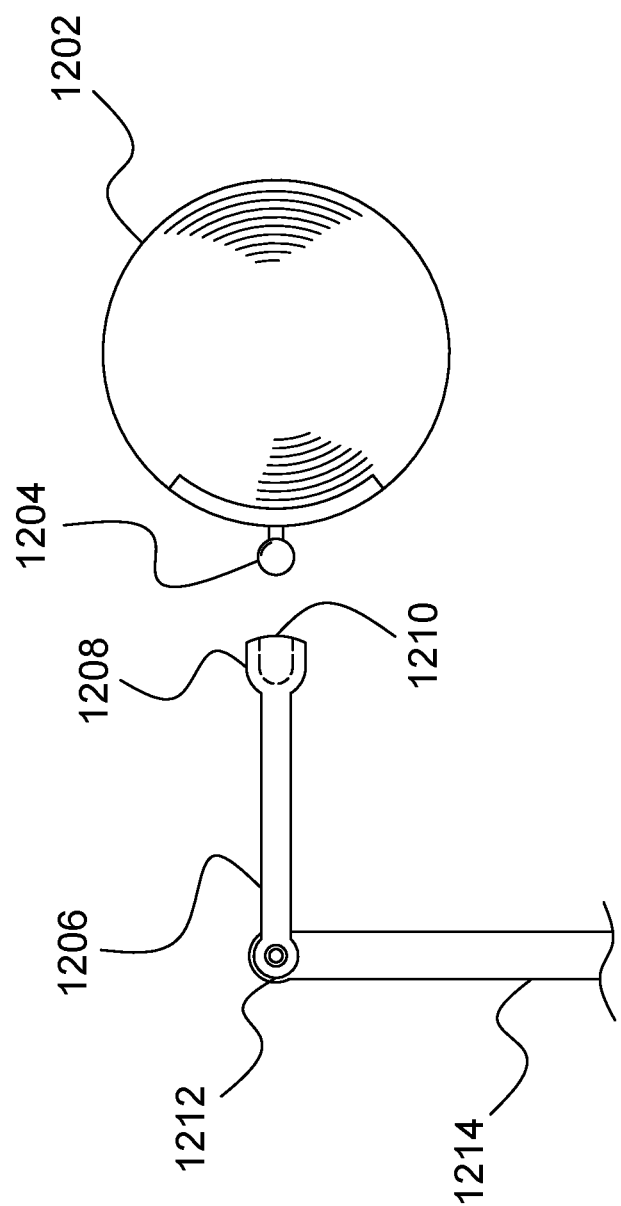
FIG. 12 shows a handle member that is configured to couple to the coupling member to couple to a digital sensor device, in accordance with some embodiments.

FIG. 12 shows a handle member 1206 that is configured to couple to the coupling member 1204 to couple to a digital x-ray sensor device 1202, in accordance with some embodiments. The handle member 1206 includes an engaging feature at an end 1208 for connecting to the coupling member 1204, such as a socket 1210 formed inside the end 1208 that is configured to retain the ball or head portion of the coupling member 1204 in the socket 1210. The socket 1201 is a hollow region in the material of the ends 1208 that can be a flexible resilient material, allowing the head of the coupling member 1204 to be inserted and removed from the socket 1210. The socket 1210 is formed such that its opening has a diameter that is slightly smaller than a diameter of the head of the coupling member 1204 to capture the head of the coupling member 1204 in the socket 1210, and allow for some movement/rotation of the head of the coupling member 1204 in the socket 1210. In some embodiments, the socket 1210 can include a slot cut on a side of the socket to allow the shaft on which the coupling member 1204 is located to pass into the slot, allowing for arm of the handle 1206 on which the socket is located to be positioned at a greater angle relative to the coupling member 1204. The portion of the handle 1206 including the socket 1210 can be joined to second portion 1214 at a hinge or joint 1212. The second portion 1214 can be coupled to an alignment structure that attaches to the x-ray source device to ensure that the x-ray source is positioned correctly with respect to the digital x-ray sensor.

Figure 20:
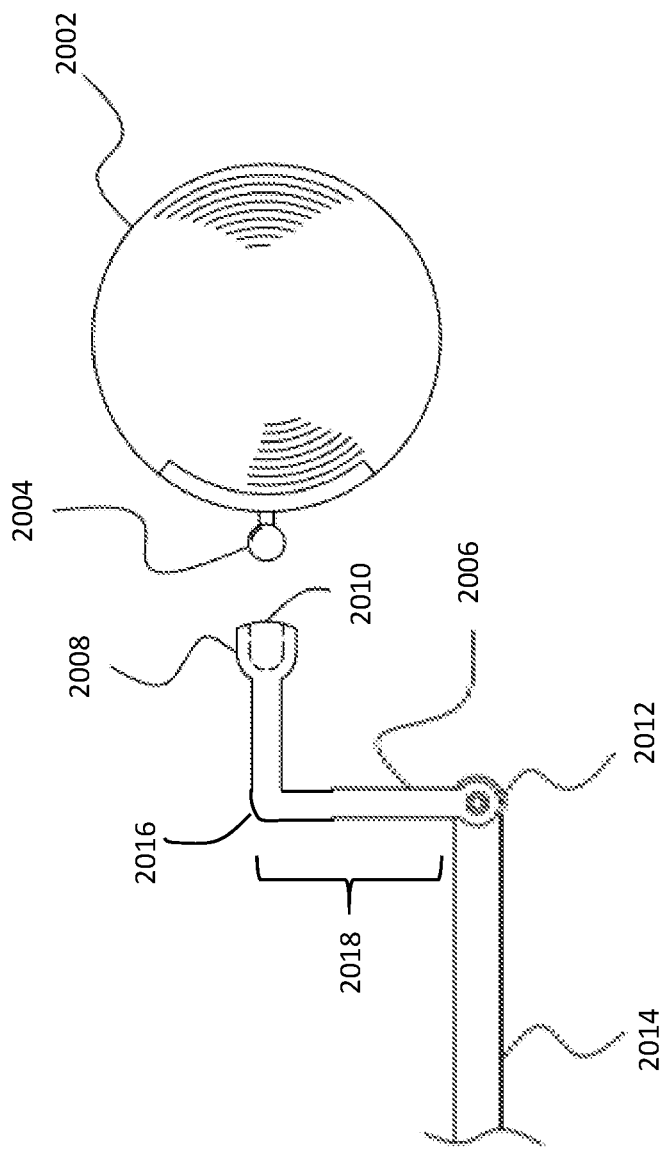
FIG. 20 shows a handle member that is configured to couple to the coupling member to couple to a digital sensor device, in accordance with some embodiments.

FIG. 20 shows a handle member 2006 that is configured to couple to the coupling member 2004 to couple to a digital x-ray sensor device 2002, in accordance with some embodiments, using an angled handle member 2006, that has a bend, such as at an elbow 2016. The elbow 2016 bends to create an offset 2018 form the second portion 2014. The offset 2018 can have a distance selected for a desired alignment of the digital x-ray sensor 2002 in a patient's mouth. As in the embodiment of FIG. 12, the handle member 2006 includes an engaging feature at an end 2008 for connecting to the coupling member 2004, such as a socket 2010 formed inside the end 2008 that is configured to retain the ball or head portion of the coupling member 2004 in the socket 2010. The socket 2010 is a hollow region in the material of the end 2008 that can be a flexible resilient material, allowing the head of the coupling member 2004 to be inserted and removed from the socket 2010. The socket 2010 is formed such that its opening has a diameter that is slightly smaller than a diameter of the head of the coupling member 2004 to capture the head of the coupling member 2004 in the socket 2010, and allow for some movement/rotation of the head of the coupling member 2004 in the socket 2010. In some embodiments, the socket 2010 can include a slot cut on a side of the socket to allow the shaft on which the coupling member 2004 is located to pass into the slot, allowing for arm of the handle 2006 on which the socket is located to be positioned at a greater angle relative to the coupling member 2004. The portion of the handle 2006 including the socket 2010 can be joined to second portion 2014 at a hinge or joint 2012. The second portion 2014 can be coupled to an alignment structure that attaches to the x-ray source device to ensure that the x-ray source is positioned correctly with respect to the digital x-ray sensor.

Figure 14:
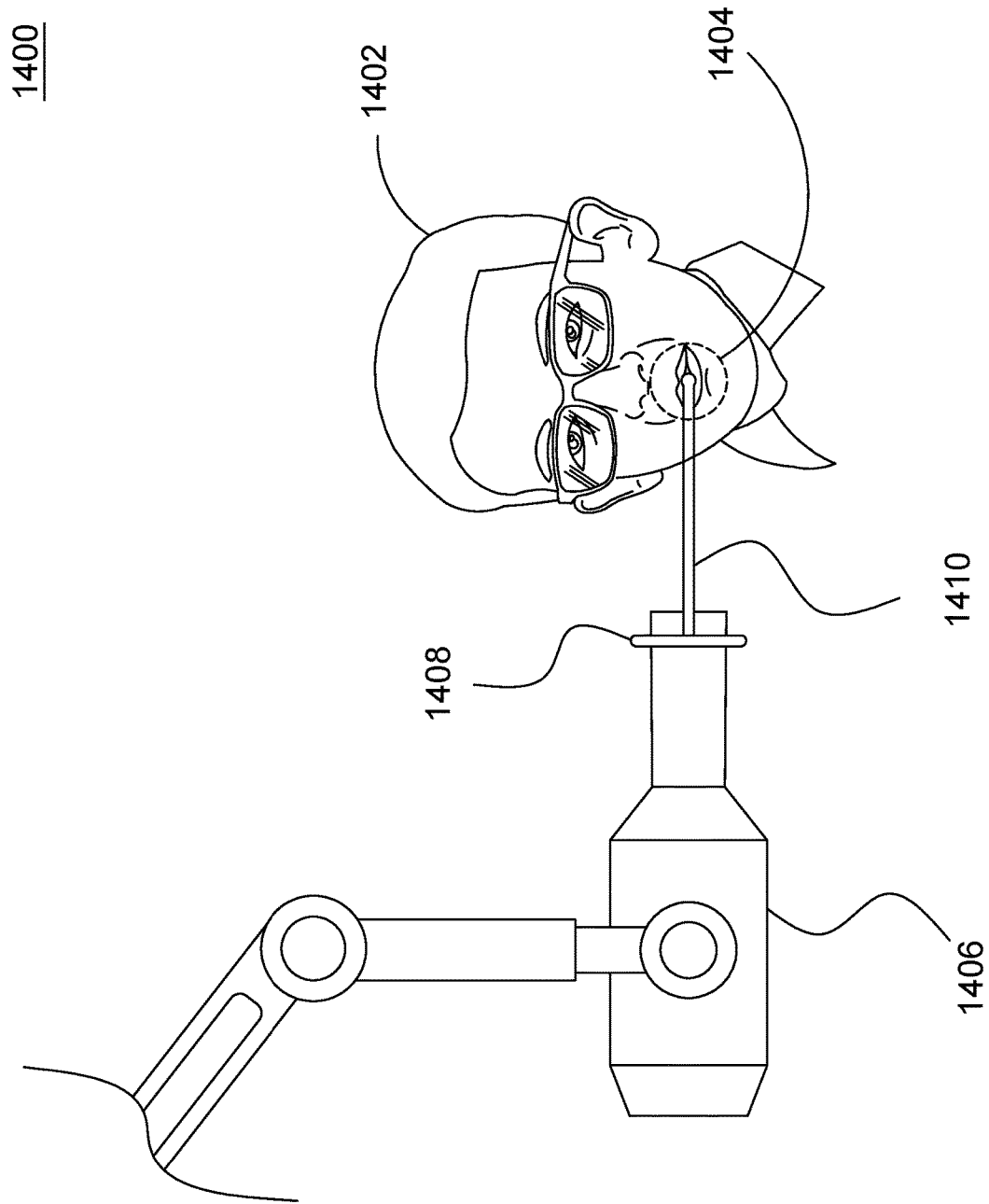
FIG. 14 shows a front view of a patient using a digital x-ray sensor, in accordance with some embodiments.

FIG. 14 shows a front view 1400 of a patient 1402 using a digital x-ray sensor 1404, in accordance with some embodiments, including a handle member 1410 coupled to an alignment structure 1408 that is further attached to the emitter of an x-ray source 1406. A handle member 1410 such as that shown in FIG. 12 can be coupled to a digital x-ray sensor 1404 that is placed in the mouth of the patient 1402. The handle member 1410, being further attached to the alignment structure 1408, which aligns the direction of the x-rays emitted by the x-ray source 1406 towards the x-ray sensor in the digital x-ray sensor 1404. The alignment structure 1408 can include a coupling ring that encircles the emitter housing, as is known.

Figure 15:
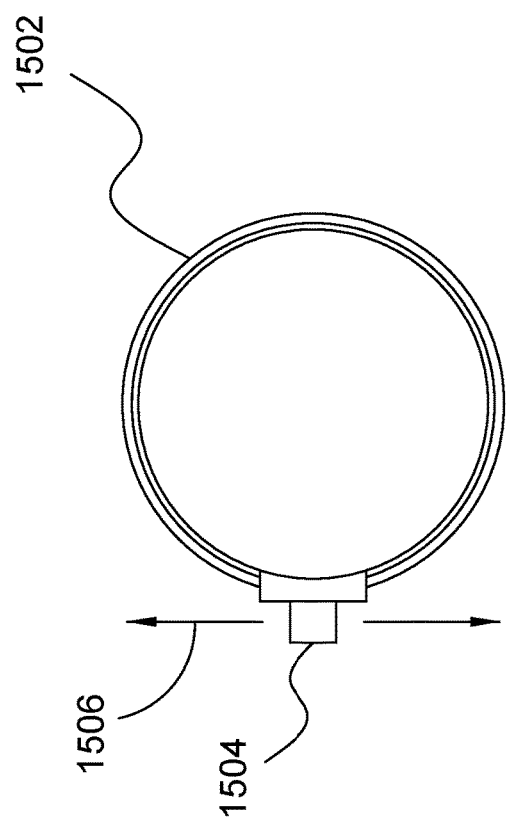
FIG. 15 shows a coupling ring for attaching a digital x-ray sensor to an x-ray source device, in accordance with some embodiments.

FIG. 15 shows a coupling ring 1500 for attaching a digital x-ray sensor to an x-ray source device, in accordance with some embodiments. The coupling ring 1502 is sized to go over the cylindrical emitter of an x-ray source, such as x-ray source 1406 of FIG. 14. The handle member attaches to an extension 1504 that extends outward from the coupling ring 1502 in a track that allows the extension 1504 to move in the track, as indicated by arrow 1506, for example. This allows the position of the attachment point of the handle to the coupling ring 1502 to be adjusted by the technician to allow optimum positioning of the x-ray source and the x-ray sensor device. In conventional devices, the coupling ring 1502 includes multiple, separate attachment points, which require the technician to remove the handle, and attach it to a different position when re-positioning the system for a different x-ray image. By providing the extension 1504 that is moveable in a track 1506 on the coupling ring 1502, the handle does not need to be disconnected from the coupling ring 1502 to reposition the handle with respect to the coupling ring 1502.

Figure 16:
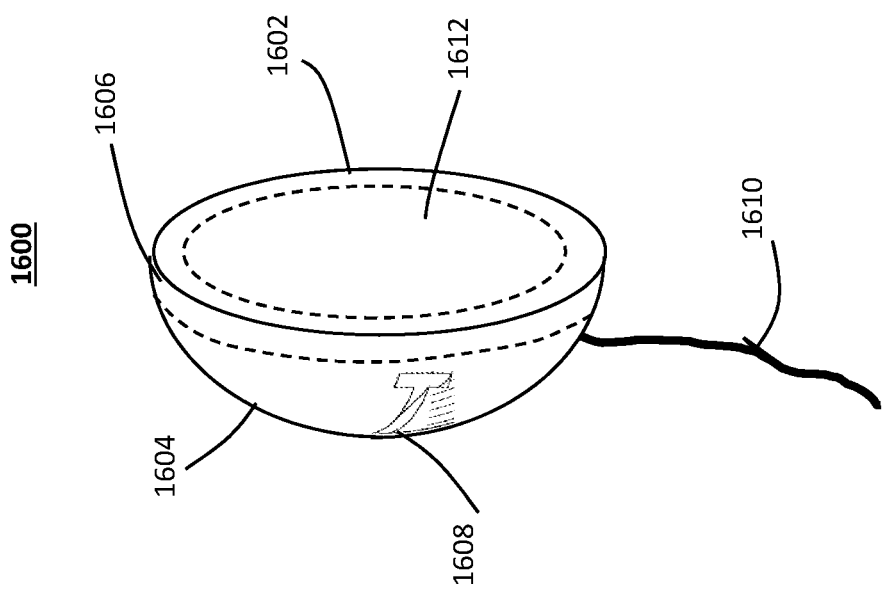
FIG. 16 shows a rounded housing of a digital x-ray sensor device in a semi-sphere configuration, in accordance with some embodiments.

FIG. 16 shows a rounded, semi-spherically configured housing 1600 of a digital x-ray sensor device in a semi-sphere configuration, in accordance with some embodiments. The semi-spherically configured housing 1600 includes a rounded, semi- or hemi-spherical portion 1602 and a flat surface 1602 that is a face formed along a plane through a sphere consistent with the semi-spherical portion 1604. That is, if the semi-spherical portion were extended to a full sphere, the flat surface 1602 passes through that sphere. The semi-spherically configured housing 1600 can further include a shoulder 1606 between the flat surface 1602 and the semi-spherical portion 1604 that extends around, or partially around the semi-spherically configured housing, adjacent to, and around the periphery of the flat surface. A handle attachment feature 1608 can be formed on an external portion of the semi-spherically configured housing, and a cable or wire assembly 1610 can connect to circuitry inside the semi-spherically configured housing 1600. The handle attachment feature 1608 can be formed substantially similar to the handle attachment features shown in FIGS. 6-12. In some embodiments a circular digital x-ray sensor 1612 can be housed inside the semi-spherically configured housing 1600, and the circular digital x-ray sensor 1612 can define a plane that is parallel with a plane of the flat surface 1602. Equivalently, the rounded housing can, instead of a semi-spherical configuration, be provided in a semi-ovoid configuration, and the flat surface 1602, rather than being circular, can be elliptically shaped or oval shaped. In some embodiments the rounded housing can be semi-spherically configured, and the flat surface 1602 can be elliptical or oval shaped. The semi-spherically configured housing 1600 can include the wire assembly 610 or cable attachment, or it can include a wireless radio transceiver and other circuitry as shown, for example, in FIG. 22.

Figure 17:
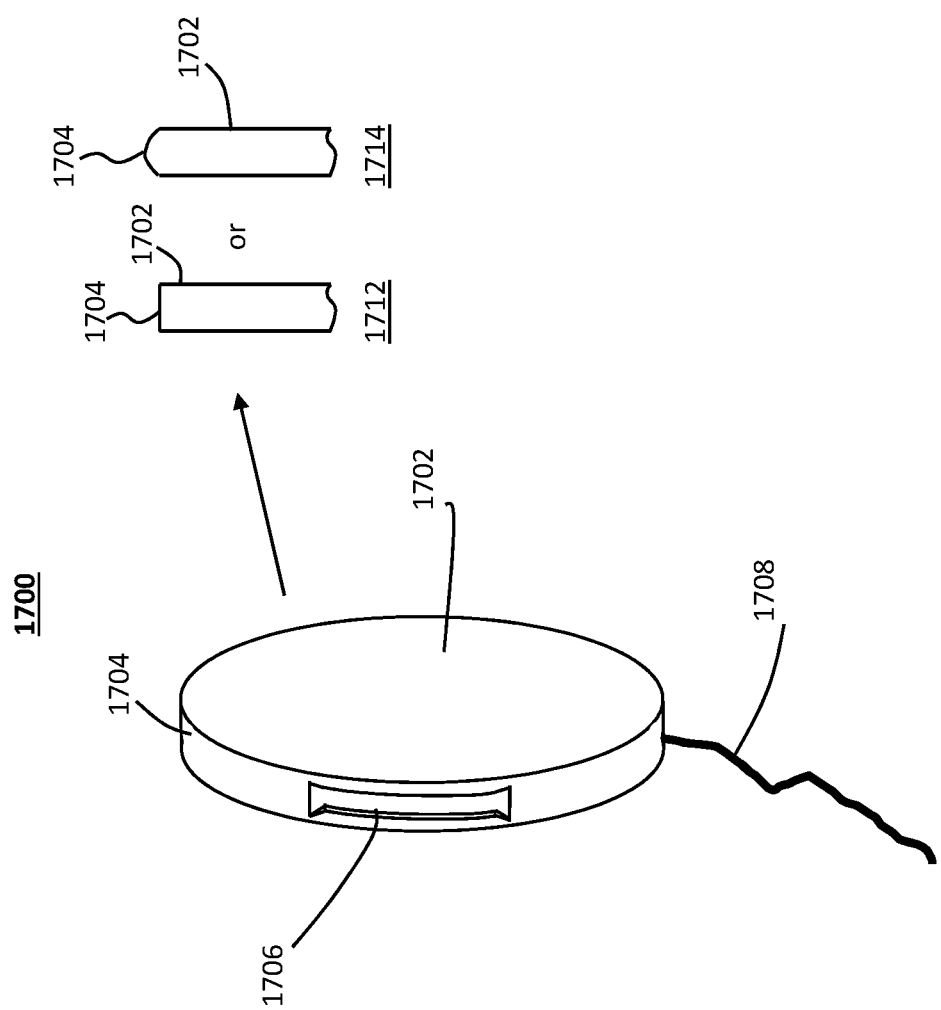
FIG. 17 shows a rounded housing of a digital x-ray sensor device in a disk configuration, in accordance with some embodiments.

FIG. 17 shows a rounded housing 1700 of a digital x-ray sensor device in a disk configuration, in accordance with some embodiments. The rounded housing 1700 here is shaped like a disk, having opposing flat surfaces such as surface 1702, and a wall 1704 around the rounded housing 1700. As shown, the rounded housing is a cylindrical shape having a height that is substantially smaller than its diameter. The flat surfaces (e.g. 1702) can be circular or elliptical or oval. The wall 1704 can be flat in a direction perpendicular to the flat surfaces as shown in side view 1712, or it can be rounded as shown in side view 1714. A handle attachment feature 1706 can be formed on the wall 1704, or on one of the opposite flat surfaces (e.g. 1702). The handle attachment feature 1706 can be formed substantially similar to the handle attachment features shown in FIGS. 6-12. A cable or wire assembly 1708 can carry signals from the digital x-ray sensor housed inside of the rounded housing 1700 to image processing and display equipment.

Figure 18:
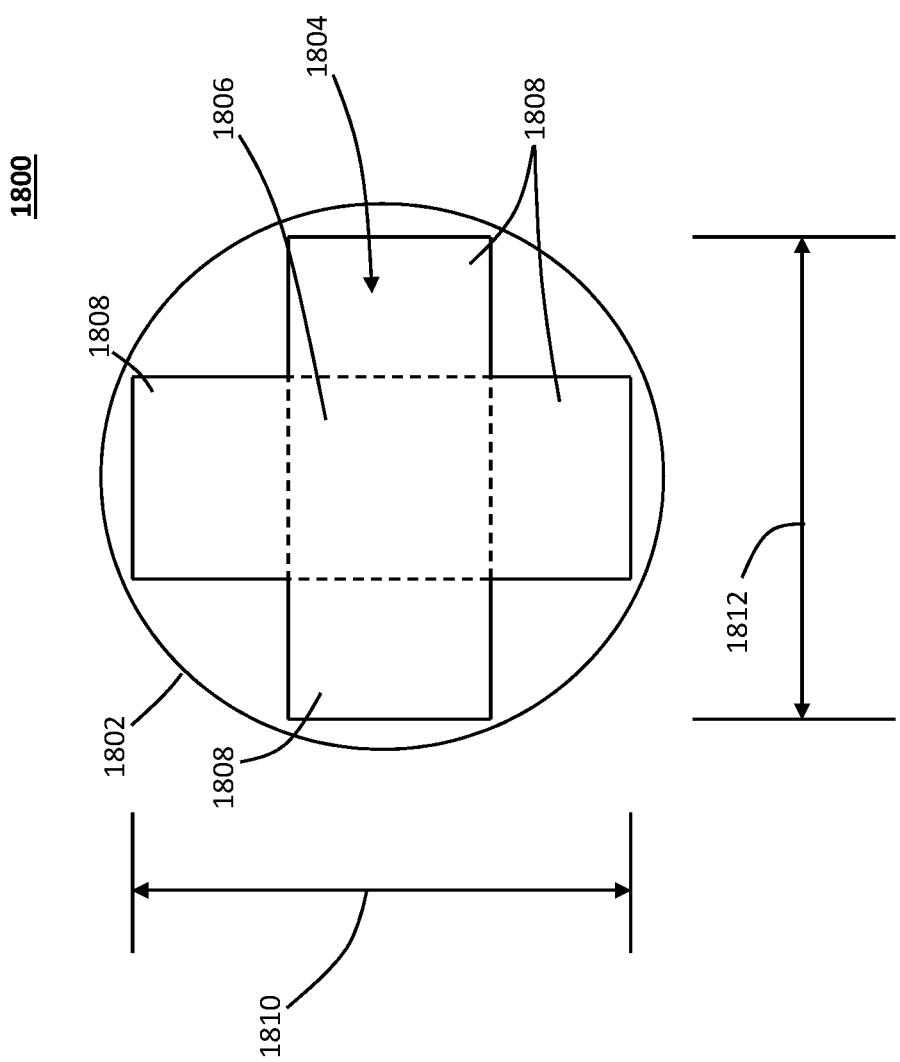
FIG. 18 shows a cross sectional view of a rounded housing having a cross-shaped digital x-ray sensor, in accordance with some embodiments.

FIG. 18 shows a cross sectional view of a rounded housing 1800 having a cross-shaped digital x-ray sensor 1804, in accordance with some embodiments. The cross-shaped digital x-ray sensor 1804 can have a central portion 1806 that is square or rectangular, with square or rectangular extensions 1808 at each side of the central portion 1806. The cross-shaped digital x-ray sensor is positioned within rounded housing 1800 within a wall 1802 of the rounded housing 1800, and can be used as an alternative to a circular digital x-ray sensor. Where the wall 1802 can vary in shape from circular, elliptical, or oval, the height 1810 and width 1812 can likewise vary to fit within the wall 1802.

Figure 19:
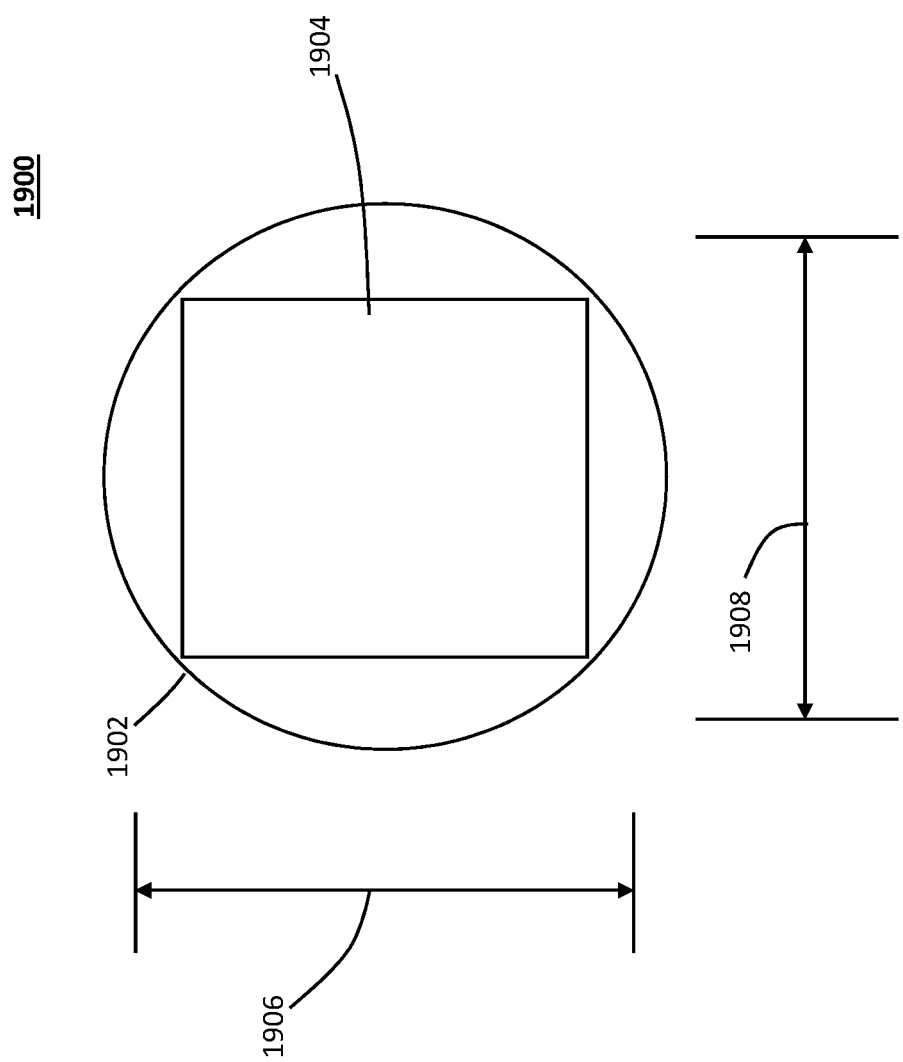
FIG. 19 shows a cross sectional view of a rounded housing having a rectangular-shaped digital x-ray sensor, in accordance with some embodiments.

FIG. 19 shows a cross sectional view of a rounded housing 1900 having a rectangular-shaped digital x-ray sensor 1904, in accordance with some embodiments. The rectangular-shaped digital x-ray sensor 1904 cane vary in height 1906 and width 1908 with a cross section shape of wall 1902 of the rounded housing 1900. That is, the rounded housing can be spherical, semi-spherical, ellipsoid, or ovoid shaped, and the height 1906 and width 1908 of the rectangular-shaped digital x-ray sensor can be configured accordingly.

Figure 21:
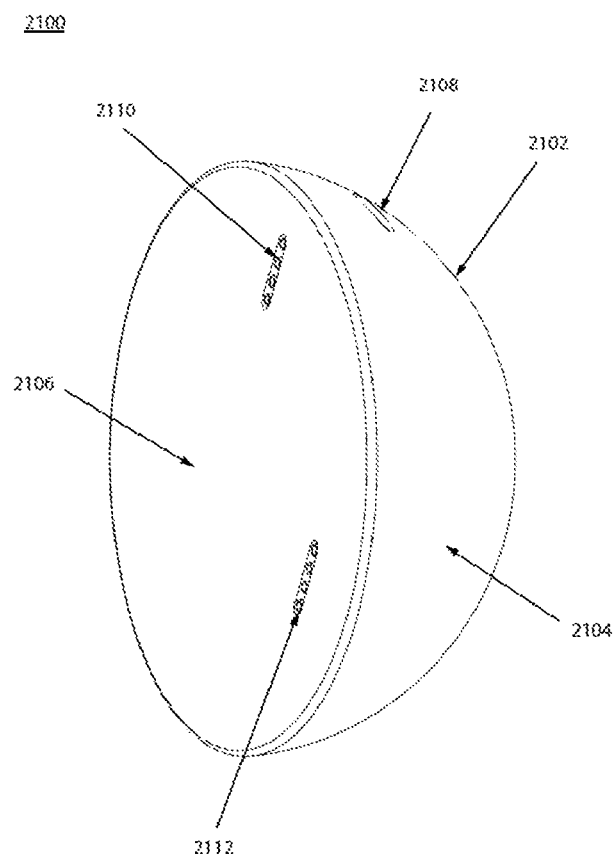
FIG. 21 shows a rounded housing of a digital x-ray sensor device in a semi-sphere configuration, having attachment features in various locations, in accordance with some embodiments.

FIG. 21 shows a rounded housing 2102 of a digital x-ray sensor device 2100 in a semi-sphere configuration, having attachment features in various locations. The housing 2102 includes a rounded semi-sphere portion 2104 and a generally flat side 2106 that is substantially circular. Several attachment slots 2110, 2112 are located on the flat face 2106. The flat slots 2110, 2112 provide both a mechanical support attachment, and an electrical signal connection. That is, disposed inside the housing at each of the attachment slots 2110, 2112 is an electrical connector to the sensor circuitry inside the rounded housing 2102. The different locations of the attachment slots 2110, 2112 allow attachment of a support and connector arm assembly at the different positions, which allow the digital x-ray sensor device 2100 to be in corresponding different orientations in the mouth of a patient. A further attachment slot 2108 on the face of the rounded semi-sphere portion 2104 can also be a mechanical and electrical connection support attachment feature to orient the digital x-ray sensor device 2100 is still another orientation.

Figure 22:
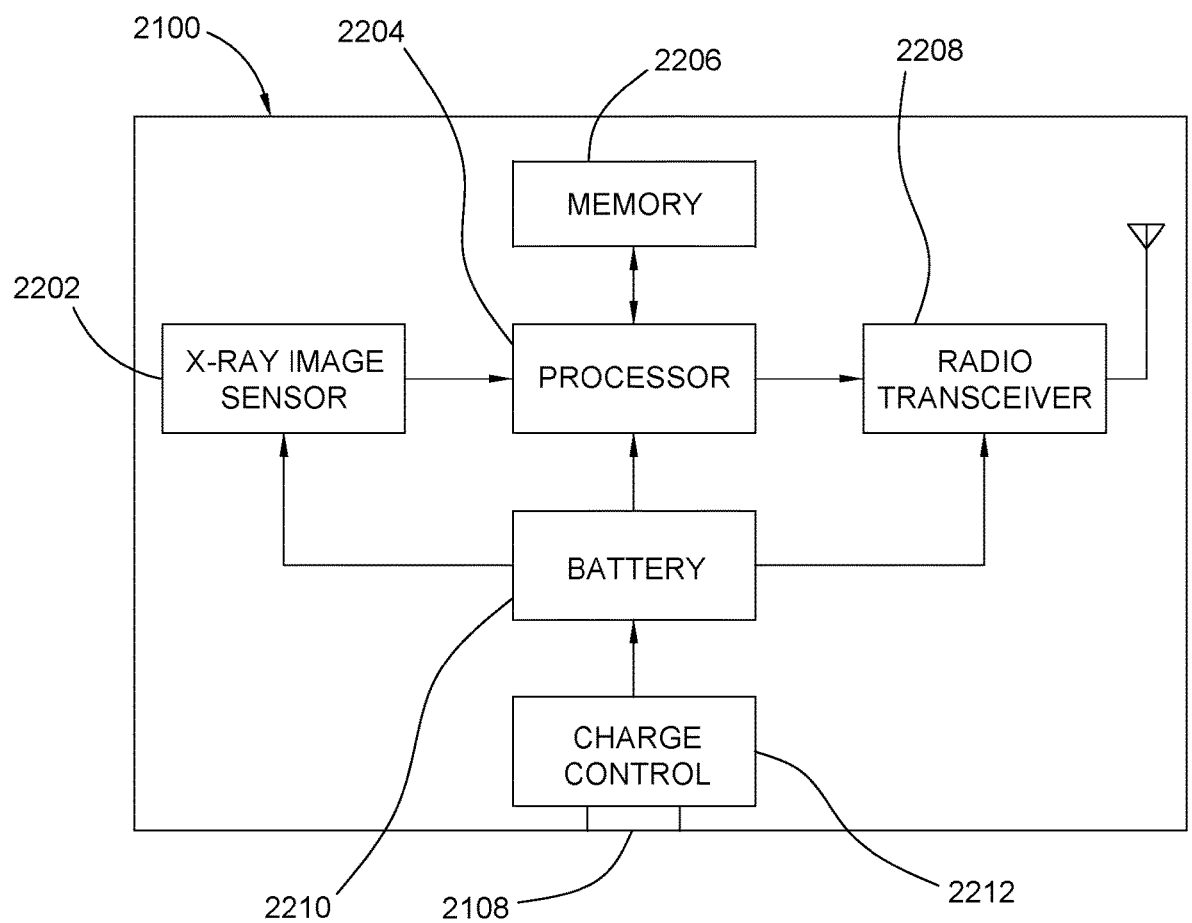
FIG. 22 shows a block schematic diagram of a digital x-ray sensor device having a wireless interface, in accordance with some embodiments.

FIG. 22 shows a block schematic diagram of a digital x-ray sensor device 2100 having a wireless interface, in accordance with some embodiments. The digital x-ray sensor device 2100 includes an x-ray image sensor 2202 that responds to x-ray emissions and produces an image data structure. The processor 2204 controls operation of the x-ray image sensor 2202, and acquires the image data from the x-ray image sensor 2202. The data can be stored in a memory 2206, which can also be used to store instruction code that is executed by the processor 2204 to perform various operations. The processor 2204 can send provide the data to a radio transceiver 2208 to transmit the data to another entity, such as a computer in the dental office. The radio transceiver can be, for example, a transceiver operated in accordance with a local or personal area wireless networking protocol, such as those defined by specification 802.11 of the Institute of Electronics and Electrical Engineers. The standards included in specification 802.11 includes those known commercially as WIFI, BLUETOOTH, ZIGBEE, and others. The radio transceiver 2208 is operated according to a known wireless interface for transmitting data and control information. The circuitry is powered by an on-board rechargeable battery 2210. A charge control circuit 2212 may be used to supervise charging operations of the battery 2210, and a connector 2108 can be used to provide a connection for providing power to the battery 2210.

Figure 23:
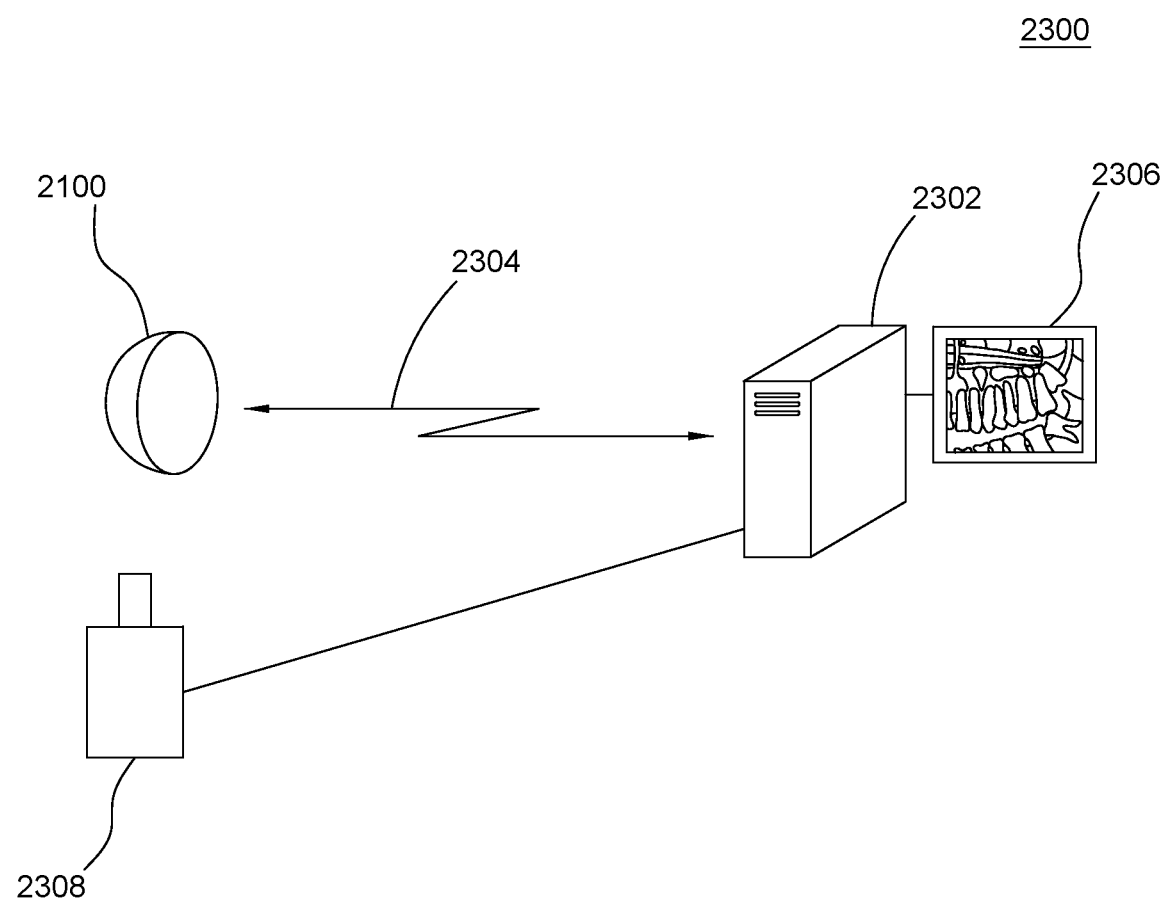
FIG. 23 shows a system using a digital x-ray sensor device having a wireless interface, in accordance with some embodiments.

FIG. 23 shows a system using a digital x-ray sensor device 2100 having a wireless interface 2304, in accordance with some embodiments. A computer 2302 or computing device can have a wireless transceiver similar to that of radio transceiver 2208 in the digital x-ray sensor device 2100 which allows the computer 2302 to communication with the digital x-ray sensor device 2100 using the wireless interface 2304. The computer 2302 can acquire image data from the digital x-ray sensor device 2100 and use the image data to render an image on a display 2306. The computer 2302 can be operated with software that causes the computer 2302 to interact with the digital x-ray sensor device 2100. The computer can be further coupled to an x-ray source 2308 in order to control the emission of x-rays onto the digital x-ray sensor device 2100.

Figure 24:
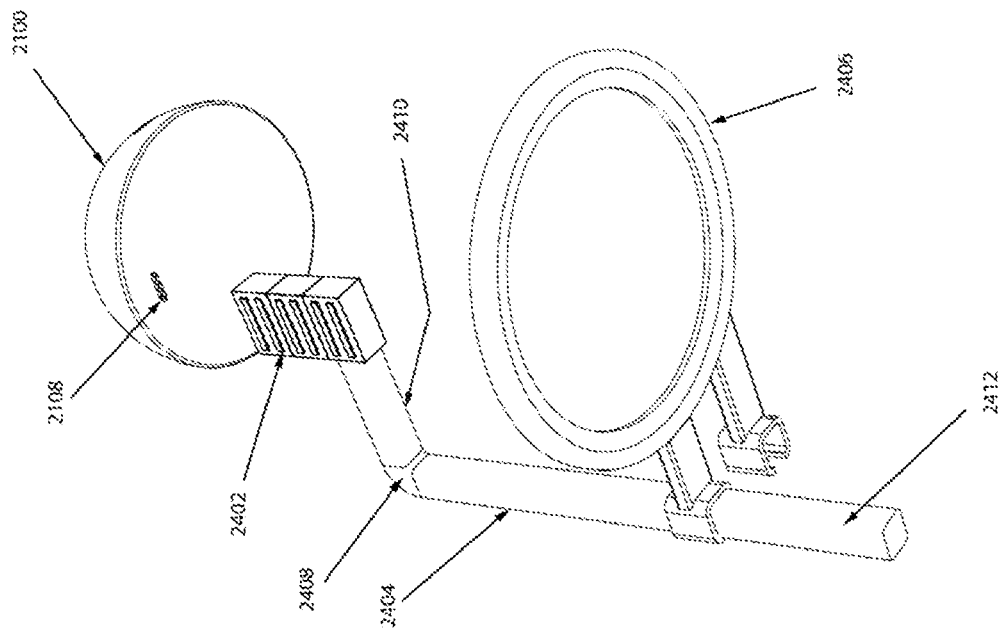
FIG. 24 shows a digital x-ray sensor device having a wireless interface used on a stabilizing arm for aligning the digital x-ray sensor device with an x-ray source, in accordance with some embodiments.
Figure 25:
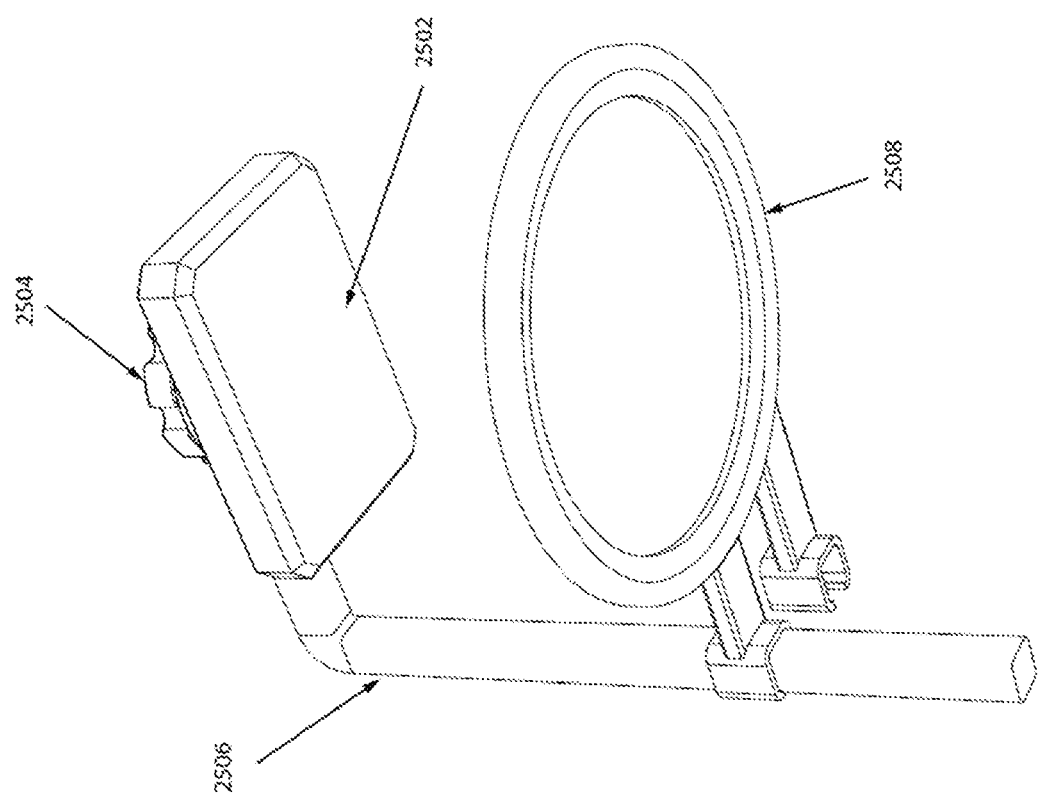
FIG. 25 shows an alternate arrangement of a digital x-ray sensor device having a swivel mount, in accordance with some embodiments.

FIG. 24 shows a digital x-ray sensor device 2100 having a wireless interface used on a stabilizing arm 2404 for aligning the digital x-ray sensor device 2100 with an x-ray source (e.g. 2308, in accordance with some embodiments. The stabilizing arm 2404 has, at one end, and connector 2402 that interfaces with the attachment slot 2110 in this view, and which is hidden by the connector 2402 here. The connector 2402 includes a portion that is inserted into the attachment slot 2110 to hold the digital x-ray sensor device 2100 in a particular orientation for obtaining x-ray images of certain teeth. Attachment slot 2108 can be used (connected to) by the connector 2402 for a different orientation of the digital x-ray sensor device 2100. To achieve different orientations, the stabilizing arm 2404 is bent at a right angle at an elbow 2408 so that the distal end 2412 of the stabilizing arm 2404 extends away from the digital x-ray sensor device 2100 at an offset so that the proximate portion 2410 of the stabilizing arm 2404 can extend from the patient's mouth. A mounting ring 2406 is coupled to the distal end 2412 of the stabilizing arm 2404, and is configured to fit onto the x-ray guide of the x-ray source, as is known. The mounting ring is offset from the distal end 2412 of the stabilizing arm 2404 by the same amount of offset provided by the proximate portion 210 of the stabilizing arm 2404 so that the x-ray source is aligned with the x-ray image sensor in the digital x-ray sensor device 2100. In some embodiments, the circuit functionality shown in FIG. 22 can be separated and distributed such that FIG. 25 shows an alternate arrangement of using a digital x-ray sensor device 2502, in accordance with some embodiments. The digital x-ray sensor device 2502 is similar to the that shown in FIG. 22, but has a rectangular housing and, rather than use attachment slots, uses a swiveling attachment provided by swivel connector 2504. The swivel connector 2504 is coupled to, and supported by the stabilizing arm 2506, and holds the digital x-ray sensor 2502 in alignment with the x-ray source in cooperation with mounting ring 2508.

Figure 26:
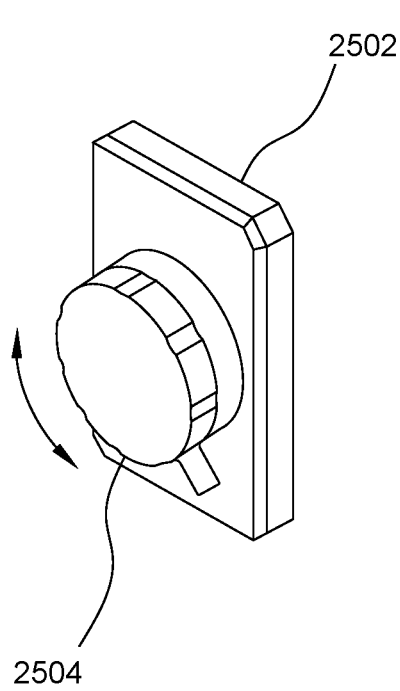
FIG. 26 shows a detail of a digital x-ray sensor device as shown in FIG. 25.
Figure 27:
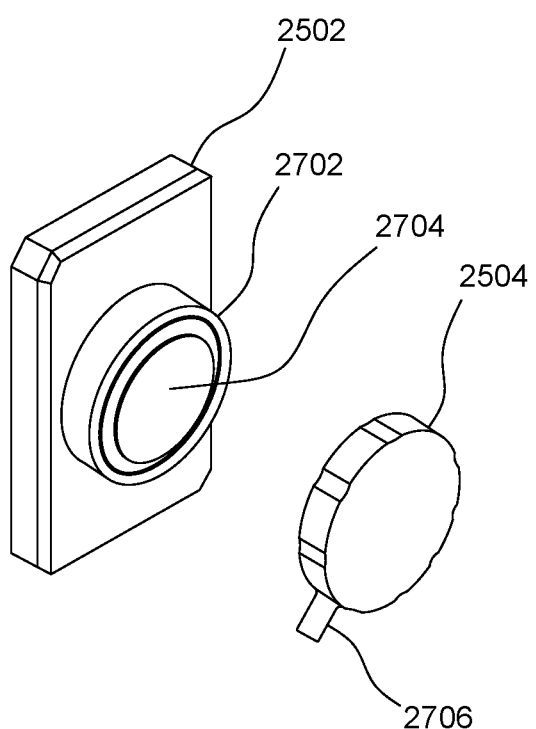
FIG. 27 shows a detail of the connection used with the digital x-ray sensor device of FIG. 25.

FIGS. 26 and 27 show a detail views of the digital x-ray sensor device 2502 as shown in FIG. 25. The swivel connector 2504 can attach magnetically to the digital x-ray sensor device 2502, which is able to swivel about the connection point, allowing an operator to adjust the orientation of the digital x-ray sensor device 2502 in the patient's mouth as desired. A magnetic interface using magnetic components 2702 and 2704, which are oppositely polarized, are attracted to similar elements on the swivel connector 2504 with corresponding polarities to align the elements together. The extension 2706 of the swivel connector can then attach to the stabilizing arm 2506.

Figure 28:
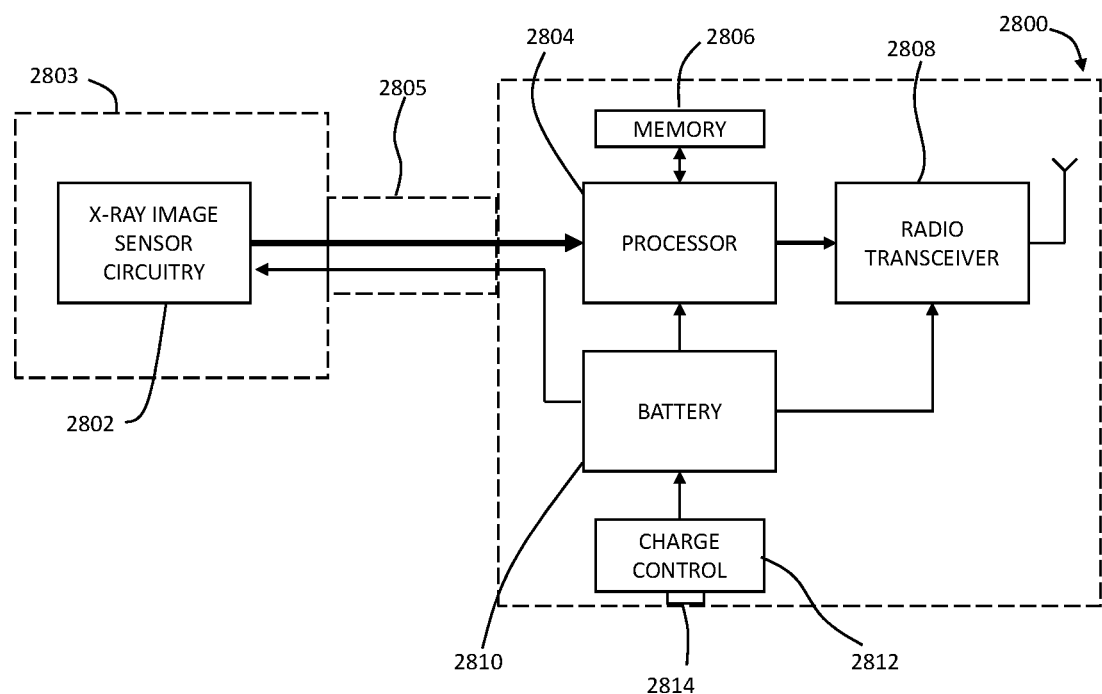
FIG. 28 shows a schematic block diagram in which the circuit functionality of the digital x-ray sensor has been separated from the communication circuitry, in accordance with some embodiments.

FIG. 28 shows a schematic block diagram in which the circuit functionality of the digital x-ray sensor has been separated from the communication circuitry, in accordance with some embodiments. Specifically, the x-ray image sensor circuit 2802 can be in a housing 2803, such as housings 102, 302/304, 402/404, 600, 1600, 1700, 1800, 1900, 2102, or device 2502. The communication module 2800 is connected to the housing 2803, and electrically to the x-ray image sensor 2802, through a connector 2805. The connector 2805 can include the mechanically interfacing elements that allow electrical signals and power to flow between the x-ray image sensor 2802 and the communications module 2800, as well as supporting structures. The communication module 2800 can include radio transceiver circuitry 2808 that is operated by a processor 2804. The radio transceiver circuitry 2808 can be configured to operate according to any of the well-known wireless networking standards, including protocols such as WiFi, BLUETOOTH, or other similar protocols. The processor 2804 can be interfaced with memory 2806 which can include non-volatile memory for storing instruction code, as well as "scratch pad" memory such as RANI for using while executing instruction code, including storing data structures such as variables, arrays, image data, and the like. In general, the processor receives image data from the x-ray sensor circuitry 2802 and then transmits the image data to a wirelessly linked computing device, substantially as shown in FIG. 23. A battery 2810 can power the other components in the communications module 2800 and the x-ray image sensor circuitry 2802. A charge control circuit 2812 can control power through an external connector or charge port 2814 to ensure the battery 2810 is properly charged.

The communications module 2800 can be implemented in a housing that is separate from the housing 2803 for the x-ray image sensor circuitry 2802. For example, the communication module 2800 can be housed in connector 2402, in stabilizing arm 2404, or even in mounting ring 2406 of FIG. 24, or any other structure that is connected to the housing 2803 and x-ray image sensor circuity 2802. If the communications module 2800 is implemented in the support arm 2406, then the connector 2805 can include, for example, connector 2402, or swivel connector 2504. If the communications module 2800 is implemented in the mounting ring 2406, or another structure connected to the support arm 2404, then the support arm 2404 would be included as part of the structure of connector 2805. Thus, the wireless communications module 2800 eliminates the need for wires or cables running between the x-ray image sensor device and the computer used to view image data produced by the x-ray image sensor device.

Figure 29A:
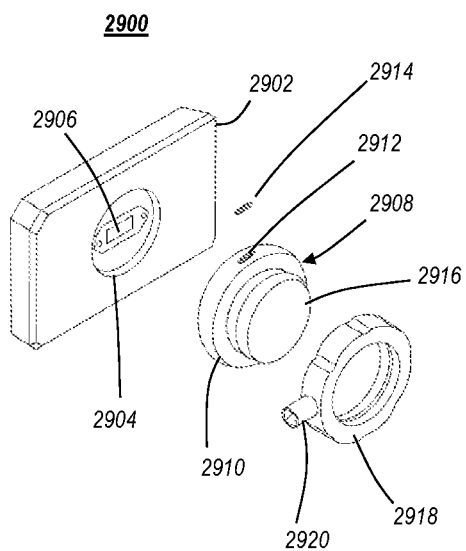
FIGS. 29A-29B show exploded views of a digital x-ray sensor and communication module system, in accordance with some embodiments.
Figure 29B:
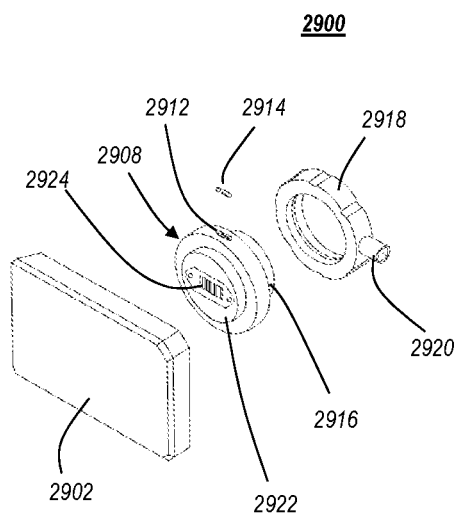

FIGS. 29A-29B show opposing exploded views of a digital x-ray sensor and communication module system 2900, in accordance with some embodiments. A digital x-ray sensor device 2902 includes a digital x-ray sensor and support circuitry to produce images in response to being irradiated with x-rays. The digital x-ray sensor device 2902 includes a port 2904 on the back side of the digital x-ray sensor device 2902 in which there is an electrical connector 2906. A communications module 2908 connects to the digital x-ray sensor 2902 at the port 2904, and has a corresponding electrical connector 2924 on a connecting portion 2922 of the communications module 2908. The communications module 2908 contains circuity substantially the same as that of communications module 2800 of FIG. 28, including a radio transceiver, battery, charge controller, and processor. The radio transceiver in the communications module 2908 can operate according to a wireless networking protocol, such as WiFi, BLUETOOTH, ZIGBEE, and so on, to wirelessly network and communicate with another device (e.g. computer 2302). The communications module 2908 further includes a charging/data port 2912 that can receive a power source connector to charge the battery contained in the communications module 2908, or the communications module 2908 can include an inductive power coil so that the battery can be charged wirelessly using inductance. A cover 2914 can fit into the charging/data port 2912 when the battery is not being charged. A mounting connector 2918 connects to the communications module 2908 and allows the communications module 2908 and digital x-ray sensor device 2902 to rotate together with respect to the mounting connector 2918, while being held by the mounting connector 2918. The mounting connector 2918 can fit over a mounting boss 2916 of the communications module 2908, and has an extension 2920 for connecting to the mounting arm 3000 of FIGS. 30A-30B. Once attached to the mounting boss 2916, the communications module 2908 is retained in the mounting connector 2918, but also able to rotate within the mounting connector 2918. Further, as shown here, the communications module 2908 is shown having a round body, exclusive of the mounting boss 2916, but the body and the connecting portion 2922 can have other shapes (e.g. square, rectangular, triangular, trapezoid, etc.). Further, it will be understood that the digital x-ray sensor device 2902 can likewise have other shapes besides the rectangular/parallelepiped shape shown here. The communications module 2908 can be removed from the digital x-ray sensor device 2902 and attached to other digital x-ray sensor devices having different form factors for different applications. In some embodiments the communications module 2908 can be more permanently attached to the digital x-ray sensor device 2902.

Figure 30A:
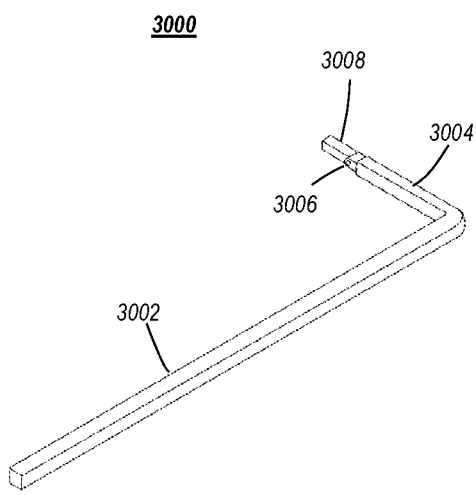
FIGS. 30A-30B show a support arm for coupling an attachment ring to a digital x-ray sensor system, in accordance with some embodiments.
Figure 30B:
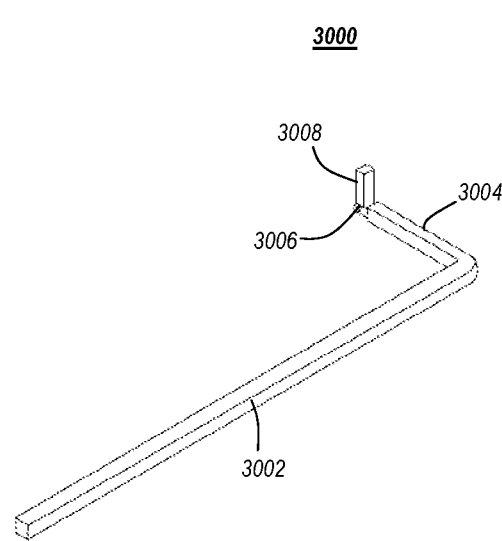

FIGS. 30A-30B show a support arm 3000 for coupling an attachment ring 3100 to a digital x-ray sensor system 2900, in accordance with some embodiments. The support arm 3000 can be substantially as shown in FIGS. 24-25 (e.g. 2404), and is generally "L" shaped having a long section 3002 and a short section 3004 that is at a substantial angle to an elongated direction of the long section 3002. At a tip if the short section 3004 can be an hinged connecting member 3008 that can move, at one end, about a hinge 3006, and which is configured to connect to the extension 2920 of the mounting connector 2918. Once the connecting member 3008 is connected to the extension 2920 the digital x-ray sensor device 2902 can be oriented as desired to capture a dental image. The hinge 3006 allows the connecting member 3008 to move, but with resistance so that when moved it will tend to stay in the position to which it has been moved.

Figure 31:
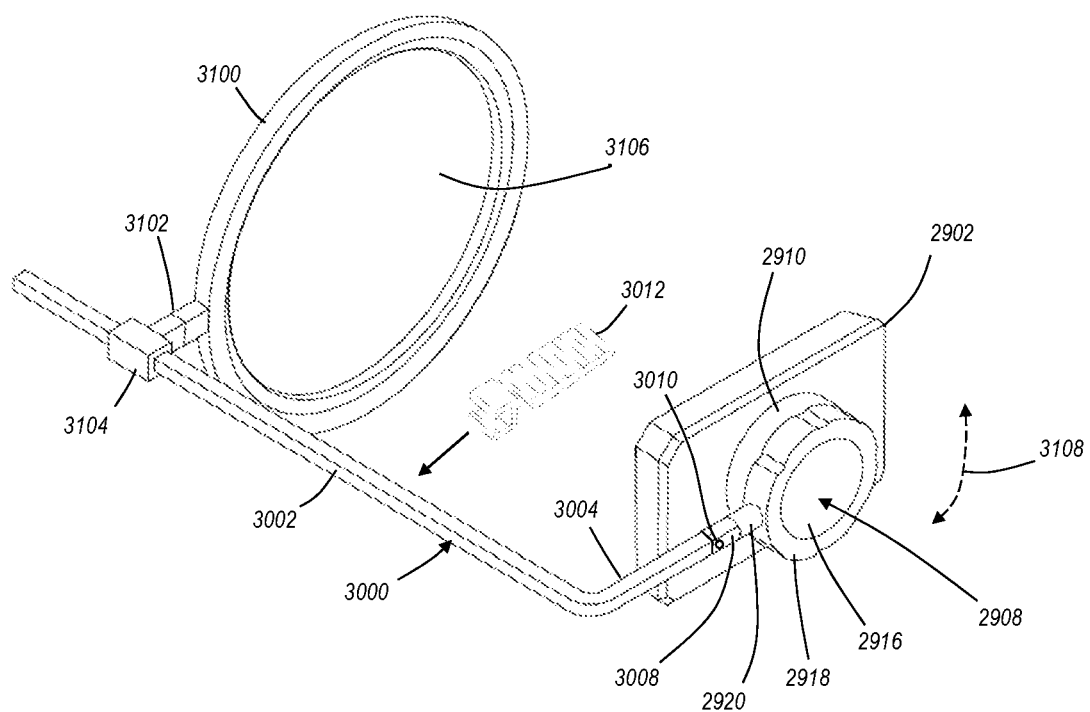
FIG. 31 shows an assembled structure for mounting a digital x-ray sensor system onto an x-ray emitter, in accordance with some embodiments.

FIG. 31 shows an assembled structure for mounting a digital x-ray sensor system 2900 onto an x-ray emitter, in accordance with some embodiments. The long section 3002 of the support arm 3000 is connected to a mounting ring 3100. The mounting ring 3100 has an extension 3102 that terminates in a slide-over connector 3104 that fits over the support arm 3000. The slide over connector 3104 allows the length between the mounting ring 3100 and the digital x-ray sensor device 2900 to be adjusted by the user. The mounting ring 3100 is sized to fit over and be retained on the cylindrical emitter of a x-ray emitter. The digital x-ray sensor device 2900 can rotate while connected to the mounting connector 2918 as indicated by arrow 3108. Thus, the user can adjust the position and orientation of the digital x-ray sensor device 2900 with respect to the x-ray emitter to capture dental images from a wide variety of angles and orientations. Once a dental image is captured by the digital x-ray sensor device 2900, the image data can be transferred to the communications module 2908 through connectors 2906, 2924, and then transmitted by the communications module 2908 to a computing device for rendering and storage. A bite block 3012 can be attached to the support arm 3000 so that a patient can bite down on the bite block, as is known.

A digital x-ray sensor device has been disclosed that houses a digital x-ray sensor in a rounded housing. The rounded housing can be spherically or ellipsoid shaped, generally, but can also include irregular portions so as not to be perfectly spherical or ellipsoid. The rounded housing lacks harsh corners, protrusion, and edges by having a minimum radius for curvature of the external surface of the rounded housing. The minimum radius can be selected to match an average radius of the curvatures of inside the mouths of people. Thus, the rounded housing provides the benefit of comfort when the digital x-ray sensor if placed in the patient's mouth compared to prior art devices that have corners and edges that cause discomfort (or worse). In some embodiments the rounded housing can house a conventional rectangular x-ray sensor, allowing the use of legacy x-ray sensors without the discomfort associated with their use. In some embodiments the rounded housing can house a similarly round or circularly configured x-ray sensor that maximizes the available cross sectional area within the rounded housing for x-ray images. The rounded housing further includes an attachment feature that allows coupling the rounded housing to a handle member for further coupling the digital x-ray sensor to an x-ray source, and ensuring a proper alignment and orientation between the x-ray source and the digital x-ray sensor to produce a particular x-ray image.

What is claimed is:

1. A dental x-ray sensor device system, comprising:
   a sensor housing configured fit in a patient's mouth, and which contains a digital x-ray sensor, wherein the sensor housing includes at least one connector;
   a support arm having a first end that is configured to connect to the at least one connector, and a second end that is configured to mount on a head of an x-ray emitter; and
   a battery powered communications module connected to the sensor housing and to the digital x-ray sensor to receive image data acquired by the digital x-ray sensor and transmit the image data, wherein the battery powered communications module is housed within the support arm.

2. The system of claim 1, wherein the second end of the support arm comprises a mounting ring that is sized to fit on the head of the x-ray emitter.

3. The system of claim 1, wherein the sensor housing is semi-spherically shaped.

4. The system of claim 1, further comprising a circular digital x-ray sensor contained in a rounded housing, and wherein the circular digital x-ray sensor conforms to an internal cross section of the rounded housing.

5. The system of claim 1, wherein the at least one connector comprises at least two connectors that allow the support arm to connect to the sensor housing such that the sensor housing has at least two different orientations.

6. The system of claim 1, wherein the rounded housing comprises an indicia that indicates an orientation of the digital x-ray sensor inside a rounded housing.

7. A digital dental x-ray sensor device system, comprising:
   a sensor housing having an external surface, the sensor housing being configured to fit within a person's mouth with the person's mouth substantially closed, wherein the sensor housing comprises a flat face t that corresponds to a plane of an digital x-ray sensor mounted in the sensor housing, the sensor housing including a plurality of attachment slots on an outside of the sensor housing;
   a wireless communications module operably connected the digital x-ray sensor that receives image data from the digital x-ray sensor and transmits the image data using a wireless networking protocol; and
   a support arm configured to attach to the sensor housing at the one of the attachment slots, wherein the communications module is housed in the support arm.

8. The digital dental x-ray sensor device system of claim 7, wherein the sensor housing is a rounded sensor housing.

9. The digital dental x-ray sensor device system of claim 8, wherein the rounded sensor housing is a spherical housing having at least one flat portion.

10. The digital dental x-ray sensor device system of claim 7, wherein the sensor housing is rectangular housing.

11. The digital dental x-ray sensor device system of claim of claim 7, wherein the sensor housing comprises at least one flat spot.

12. The digital dental x-ray sensor device system of claim 7, wherein the digital x-ray sensor has a circular shape.

13. The digital dental x-ray sensor device system of claim 7, wherein the support arm is configured to attach to the sensor housing at a first end of the support arm, the support arm further having a mounting ring at a second end of the support arm that is configured to fit on a head of an X-ray emitter, and wherein the communications module is housed in within the mounting ring.

14. The digital dental x-ray sensor device system of claim 7, wherein the support arm includes a mounting ring portion that is configured to attach to a head of an x-ray emitter.

15. A dental x-ray sensor device, comprising:
a sensor housing configured fit in a patient's mouth, and which contains a digital x-ray sensor, wherein the sensor housing includes at least two connectors;
a support arm having a first end that is configured to alternatively connect to one of each of the at least two connectors, and a second end that is configured to mount on a head of an x-ray emitter, wherein the at least two connectors are each located at different positions on the sensor housing to allow at least two different orientations of the sensor housing when connected to the first end of the support arm; and
a battery powered communications module connected to the sensor housing and to the digital x-ray sensor to receive image data acquired by the digital x-ray sensor and transmit the image data.

16. The dental x-ray sensor device of claim 15, wherein the battery powered communications module is housed within the support arm.

17. The dental x-ray sensor device of claim 15, wherein the second end of the mounting arm comprises a mounting ring that is sized to fit on the head of the x-ray emitter, and wherein the communications module is housed within a mounting ring.

18. The dental x-ray sensor device of claim 15, wherein the sensor housing is semi-spherically shaped.

19. The dental x-ray sensor device of claim 15, further comprising a circular digital x-ray sensor contained in a rounded housing, and wherein the circular digital x-ray sensor conforms to an internal cross section of the rounded housing.

20. The dental x-ray sensor device of claim 15, wherein the rounded housing comprises an indicia that indicates an orientation of the digital x-ray sensor inside a rounded housing.

* * * * *